(12) United States Patent
Lichkus et al.

(10) Patent No.: US 6,488,503 B1
(45) Date of Patent: Dec. 3, 2002

(54) PROSTHETIC TEETH AND METHOD OF MAKING THEREFOR

(75) Inventors: Andrew M. Lichkus, York, PA (US); Wayne C. Bollinger, York, PA (US); Scott E. Shaffer, Jacobus, PA (US)

(73) Assignee: Dentsply Research & Development Corp.

( * ) Notice: Subject to any disclaimer, the term of this patent is extended or adjusted under 35 U.S.C. 154(b) by 51 days.

(21) Appl. No.: 09/734,867

(22) Filed: Dec. 12, 2000

Related U.S. Application Data

(60) Provisional application No. 60/171,336, filed on Dec. 21, 1999.

(51) Int. Cl.[7] .................................................. A61C 13/08
(52) U.S. Cl. ...................................... 433/202.1; 264/19
(58) Field of Search .......................... 433/202.1, 203.1, 433/212.1; 264/19, 20; 106/35

(56) References Cited

U.S. PATENT DOCUMENTS

| | | | |
|---|---|---|---|
| 2,380,568 A | 7/1945 | Adams | 85/5 |
| 2,454,847 A * | 11/1948 | Slack, Jr. | 433/202.1 |
| 2,463,550 A * | 3/1949 | Myerson et al. | 433/202.1 |
| 2,514,075 A | 7/1950 | Kelly | 32/8 |
| 2,517,100 A | 8/1950 | Erdle | 18/55.1 |
| 2,528,219 A * | 10/1950 | Feagin | 433/202.1 |
| 2,643,455 A | 6/1953 | Budish | 32/8 |
| 2,677,150 A | 5/1954 | Rydin | 18/55.1 |
| 2,678,470 A | 5/1954 | Slack, Jr. | 18/55.1 |
| 3,126,429 A | 3/1964 | Saffir | 264/20 |
| 3,218,711 A | 11/1965 | Connan | 32/8 |
| 3,628,248 A * | 12/1971 | Kroder et al. | 433/202.1 |
| 3,861,044 A | 1/1975 | Swinson, Jr. | 32/17 |
| 4,324,546 A | 4/1982 | Heitlinger | 433/25 |
| 4,392,829 A | 7/1983 | Tanaka | 433/222 |
| 4,396,476 A | 8/1983 | Roemer et al. | 204/159.16 |
| 4,433,959 A | 2/1984 | Faunce | 433/201 |
| 4,436,684 A | 3/1984 | White | 264/138 |
| 4,481,227 A | 11/1984 | Tanaka | 427/2 |
| 4,575,805 A | 3/1986 | Moermann et al. | 364/474 |
| 4,611,288 A | 9/1986 | Duret et al. | 364/474 |
| 4,615,678 A | 10/1986 | Moermann et al. | 433/201.1 |
| 4,617,159 A | 10/1986 | Miller | 264/16 |
| 4,645,454 A | 2/1987 | Amdur et al. | 433/199.1 |
| 4,650,418 A | 3/1987 | Blair et al. | 433/203.1 |
| 4,663,720 A | 5/1987 | Duret et al. | 364/474 |
| 4,681,633 A | 7/1987 | Watanabe et al. | 106/35 |
| 4,722,689 A | 2/1988 | Corbett | 433/218 |
| 4,742,464 A | 5/1988 | Duret et al. | 364/474 |
| 4,747,776 A * | 5/1988 | Sudderth | 433/202.1 |
| 4,766,704 A | 8/1988 | Brandestini et al. | 51/327 |
| 4,837,732 A | 6/1989 | Brandestini et al. | 364/413.28 |
| 4,970,032 A | 11/1990 | Rotsaert | 264/20 |
| 5,089,306 A | 2/1992 | Grossman et al. | 428/35.1 |
| 5,127,834 A | 7/1992 | Hasegawa et al. | 433/202.1 |
| 5,151,044 A | 9/1992 | Rotsaert | 433/229 |
| 5,308,243 A | 5/1994 | Emmons | 433/203.1 |
| 5,342,201 A | 8/1994 | Oden | 433/223 |
| 5,346,397 A * | 9/1994 | Braiman | 433/202.1 |
| 5,452,219 A | 9/1995 | Dehoff et al. | 364/474.05 |
| 5,502,087 A * | 3/1996 | Tateosian et al. | 433/202.1 |
| 5,989,031 A | 11/1999 | Kura et al. | 433/202.1 |

* cited by examiner

*Primary Examiner*—Todd E. Manahan
(74) *Attorney, Agent, or Firm*—Dale R. Lovercheck; James B. Bieber

(57) ABSTRACT

A process for producing an artificial tooth comprising: injection molding polymerizable material into a mold to form an outer external polymeric layer. Then injection molding polymerizable material into the mold to form an inner polymeric layer applied on the first external layer. Then injection molding polymerizable material into the mold to form a solid core applied on the inner external layer.

18 Claims, 14 Drawing Sheets

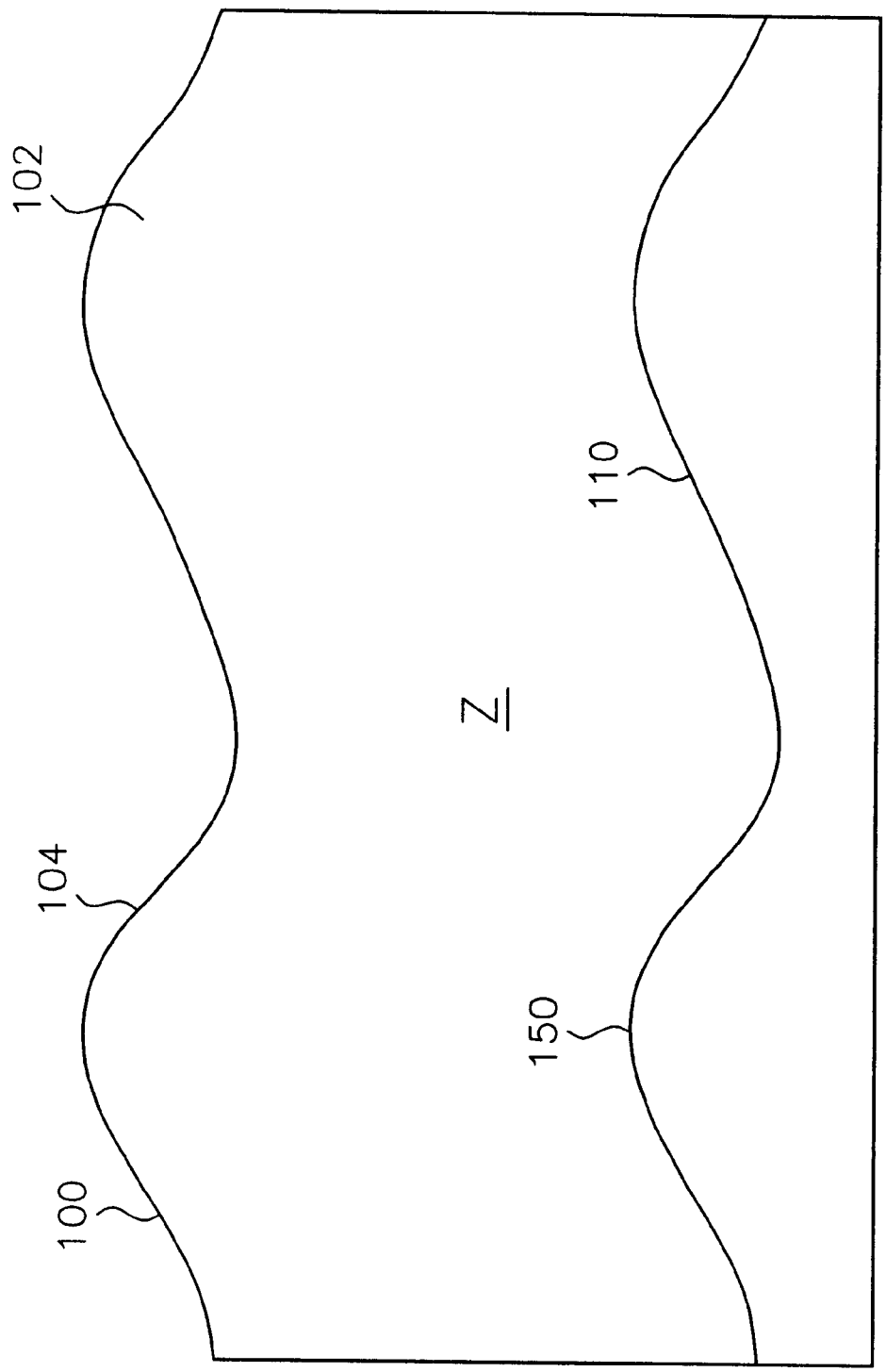

PROSTHETIC TEETH AND METHOD OF MAKING THEREFOR

This application claims the benefit of U.S. Provisional patent application No. 60/171,336 filed Dec. 21, 1999.

The invention relates to injection molding of polymerizable material to form prosthetic teeth of polymeric material consisting of several layers.

BACKGROUND OF THE INVENTION

Dehoff et al, the disclosure of which is incorporated herein by reference in its entirety, disclose prosthetic teeth. Roemer, et al. in U.S. Pat. No. 4,396,476 ,and U.S. patent application Ser. No. 09/333,727 filed Jun. 15, 1999 the disclosures of which are incorporated herein by reference in their entirety, disclose polymerizable tooth making compositions. Kura et al in U.S. Pat. No. 5,989,031, the disclosure of which is incorporated herein by reference in its entirety, disclose injection molding of thermoplastic to form a tooth. According to DIN 13914, artificial teeth for producing dental prostheses must consist of several layers because of the desired similarity to natural teeth. Such multilayer teeth have previously been produced exclusively by a pressing process, wherein the differently dyed pressing masses are placed by hand in the pressing tool. The pressing of the teeth is very labor-intensive. The distribution of the layers put in place by hand is subject to irregularities. The excess amounts necessary for pressing lead to considerable burr formation at the separating plane of the mold halves. This makes subsequent processing necessary. Thus considerable production effort is connected to the production of conventional multilevel teeth, so that these teeth are relatively expensive.

The present invention is based on the problem of creating an artificial tooth constructed of several layers whose production can be largely automated and in which a reproducible arrangement of layers is guaranteed and, in particular, burr formation is also minimized, so that low production costs result.

The invention provides multiple part dental tooth molds and prosthetic teeth with an enamel layer having zones of uniform thickness. Prosthetic teeth in accordance with a preferred embodiment of the invention are readily articulable within sets and proportionally consistent within families. Prosthetic teeth in accordance with the invention are useful for making full and/or partial dentures, and as crowns, implant teeth and shade guides having prosthetic teeth thereon.

Tooth molds are used in the dental industry for the manufacture of artificial teeth. Refining steps include a final finish-polish step, which provides a mold of high-definition of the surface properties of the artificial tooth to be produced by molding tooth making material therein.

Dehoff et al in U.S. Pat. No. 5,452,219 (Case 1619) discloses a method for making a tooth mold. Erdle in Australia 124,083 disclose ceramic articles and material and method for coloring or shading the same. Saffir in U.S. Pat. No. 2,380,568 disclose artificial tooth. Kelly in U.S. Pat. No. 2,514,075 disclose artificial tooth. Erdle in U.S. Pat. No. 2,517,100 disclose method of forming ceramic articles and producing different colors or shades along different potions of the article. Budish in U.S. Pat. No. 2,643,455 disclose artificial teeth. Rydin in U.S. Pat. No. 2,677,150 disclose method in producing artificial teeth. Slack, Jr. in U.S. Pat. No. 2,678,470 disclose polymerizing method. Saffir in U.S. Pat. No. 3,126,429 disclose method of casting teeth having different colored layers. Connan in U.S. Pat. No. 3,218,711 disclose artificial teeth. Swinson in U.S. Pat. No. 3,861,044 teaches a method of fitting a tooth with a dental inlay. Heitlinger et al. in U.S. Pat. No. 4,324,546 disclose an apparatus and method for the manufacture of dentures. Tanaka in U.S. Pat. No. 4,392,829 disclose metal porcelain dental restoration and method of making. Faunce in U.S. Pat. No. 4,433,959 disclose composite laminate dental veneer containing color systems. White in U.S. Pat. No. 4,436,684 describes methods of making three dimension models and mold cavities of internal body structure.

Tanaka in U.S. Pat. No. 4,481,227 disclose method of coloring bakable porcelain dental restorations. Moermann et al. in U.S. Pat. No. 4,575,805 disclose a method and a apparatus for the fabrication of custom-shaped implants. Duret et al. in U.S. Pat. No. 4,611,288 describe a system for taking an impression of a body region for the production of a prosthesis.

Moermann et al. in U.S. Pat. No. 4,615,678 teach a blank from which an implant can be machined by an apparatus of the type disclosed in U.S. Pat. No. 4,575,805. Miller in U.S. Pat. No. 4,617,159 disclose method of molding a dental shade sample. Amdur et al. in U.S. Pat. No. 4,645,454 disclose porcelain products and methods. Blair et al. in U.S. Pat. No. 4,650,418 disclose dental restoration shading. Duret et al. in U.S. Pat. Nos. 4,663,720 and 4,742,464 disclose a method of making a dental prosthesis. Watanabe et al. in U.S. Pat. No. 4,681,633 disclose high strength calcium phosphate glass ceramic materials. Corbett in U.S. Pat. No. 4,722,689 disclose coated temporary dental crowns. Brandestini et al. in U.S. Pat. No. 4,766,704 describe a method and apparatus for machining a custom-shaped dental restorative part from a blank of dental material in a single operation. Brandestini et al. in U.S. Pat. No. 4,837,732 teach a method of facilitating acquisition of data defining the three-dimensional shape of prepared teeth and their immediate vicinity.

Rotsaert in U.S. Pat. No. 4,970,032 disclose processes for the manufacture of artificial teeth and crowns. Grossman et al. in U.S. Pat. No. 5,089,306 disclose glazing dental constructs. Hasegawa et al. in U.S. Pat. No. 5,127,834 disclose artificial teeth and method for making them. Rotsaert in U.S. Pat. No. 5,151,044 disclose blanks for the manufacture of artificial teeth and crowns. Emmons in U.S. Pat. No. 5,308,243 disclose method and compositions for producing lifelike dental porcelain restorations and dental porcelain restorations so produced. Oden in U.S. Pat. No. 5,342,201 disclose method of manufacturing ceramic artificial tooth restorations.

It is an object of the invention to provide artificial teeth with an enamel layer having zones of constant thickness.

It is an object of the invention to provide a family of prosthetic teeth, including a first tooth in a first set of teeth having a first overall labial length, and a first back length, and a second tooth in a second set of teeth having a second overall labial length, and a second back length, wherein the ratio of the first to the second overall labial length is substantially equal to the ratio of the first to the second back length.

It is an object of the invention to provide a prosthetic tooth including a tooth body having two generally symmetrical curved grooves between three curved ridges on the labial face of the body at the incisal end of the body, wherein the grooves are deepest at the incisal end and extend substantially from the incisal edge to at least about 15 percent of the overall tooth length.

It is an object of the invention to provide an image of at least a portion of at least one upper tooth and at least one lower tooth, each said tooth being from the same side of the same set of teeth, modifying initial data corresponding to the image to form modified data, molding modified prosthetic teeth in molds made using the modified data, whereby, during articulation the modified prosthetic teeth contact along a larger proportion of tooth surface than prosthetic teeth made in molds using the initial data.

Set of teeth as used herein refers to teeth to be used for the same individual, such as is a single denture whether full or partial.

Family of teeth as used herein refers to sets of teeth of different sizes and/or shades but having common shapes.

SUMMARY OF THE INVENTION

A process for producing an artificial tooth comprising: injection molding polymerizable material into a mold to form an outer external polymeric layer. Then injection molding polymerizable material into the mold to form an inner polymeric layer applied on the first external layer. Then injection molding polymerizable material into the mold to form a solid core applied on the inner external layer.

The problems of high mold pressure and limited tooth shading are solved according to the invention in that low pressure is use for injection and shading may be custom blended at the molding site.

The invention relies upon the recognition that a considerable savings in cost can be achieved by injection molding technology, since injection molding is done completely automatically and hence a reproducible arrangement of layers can be guaranteed. This may involve a multicomponent injection molding process, wherein the material components form layers inside the tooth body so that, by dying the individual material components differently the natural tooth appearance can be optimally approximated.

A prosthetic tooth having an enamel layer which has a zone of substantially constant thickness. This tooth is molded using a dental tooth mold part prepared by imaging a dental pattern of a prosthetic tooth shade layer and/or shader mold part outer surface, and forming the dental pattern in a mold by program directed milling.

The invention provides a family of prosthetic teeth, including a first tooth in a first set of teeth has a first overall labial length, and a first back length, and a second tooth in a second set of teeth has a second overall labial length, and a second back length. The ratio of the first overall labial length to the second overall labial length is substantially equal to the ratio of the first back length to the second back length. Preferably the first tooth has a first shade length and the second tooth has a second shade length and the ratio of the first shade length to the first overall labial length is substantially equal to the ratio of the second shade length to the second overall labial length.

The invention provides a prosthetic tooth including a tooth body having two generally symmetrical curved grooves between three curved ridges on the labial face of the body at the incisal end of the body. The grooves are deepest at the incisal end and extend substantially from the incisal edge to at least about 15 percent of the overall tooth length.

The invention provides a method of making readily articulable prosthetic teeth by displaying an image of at least a portion of at least one upper tooth and at least one lower tooth from the same side of the same set of teeth, then modifying initial data corresponding to the image to form modified data, molding readily articulable prosthetic teeth in molds made using the modified data, whereby, during articulation the readily articulable prosthetic teeth contact along a larger proportion of tooth surface than prosthetic teeth made in molds using the initial data.

BRIEF DESCRIPTION OF THE DRAWINGS

The invention will be discussed in greater detail on the basis of the embodiments show in the attached drawings. These show in FIG. 1 a section in the sagittal plane through an artificial tooth constructed according to the invention as a front tooth;

FIG. 6A is a partial schematic side view of a prosthetic tooth in accordance with the invention.

DETAILED DESCRIPTION OF PREFERRED EMBODIMENT

Figure 1:
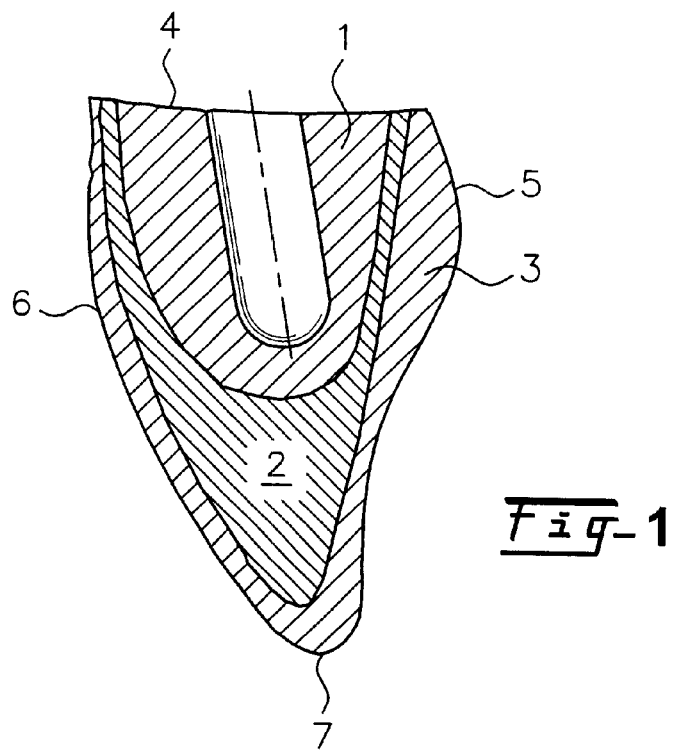

In the figures, identical features of the artificial tooth according to the invention are labeled with the same reference numerals.

Figure 2:
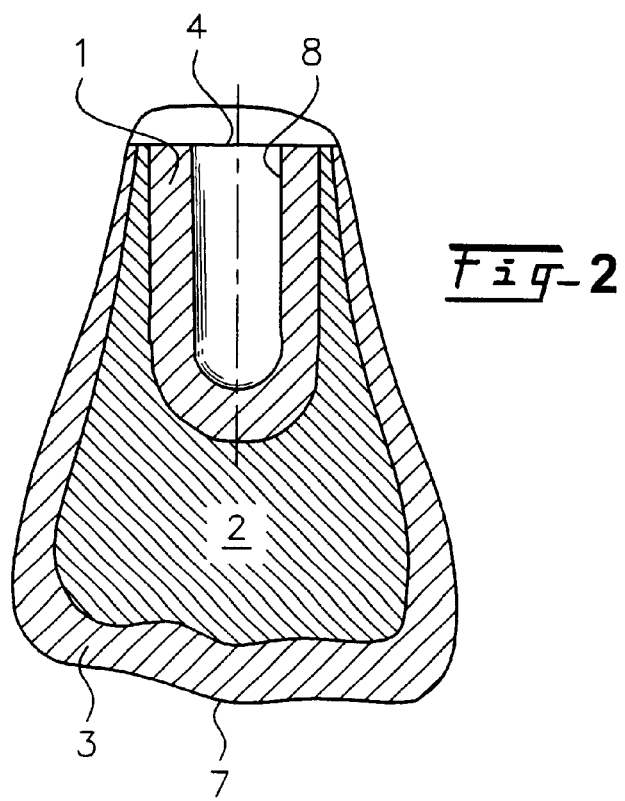
FIG. 2 a section in the frontal plane through the tooth of FIG. 1.

As is seen from FIGS. 1 and 2, a tooth according to the invention consists of a tooth body with a solid core 1. The solid core 1 forms the basic element of the tooth, on which the additional external layers 2 and 3 are built up. In this respect, the basal side 4 of the solid core 1 remains bare, whereas the palatal side 5, the labial side 6 and the incisal side 7 of the tooth are formed by the external layers 2,3. The solid core 1 is constructed roughly in the shape of a truncated cone, with the side opposite the basal side 4 being rounded off. The external layer 2 directly enveloping the solid core 1 is formed with a small thickness in the area of the edge of the basal side 4, the tooth base, shaped with a small thickness, which amounts to 0.2 mm, for example. In the direction towards the incisal side 7 of the tooth, however, the external layer 2 increases considerably in thickness and is also shaped such that, together with the solid core 1, it practically forms the basic structure of the tooth. The outermost external layer 3 has essentially the same thickness around the periphery, with the palatal side 5 additionally modeled by the external layer 3, as shown, while the external layer 3 has roughly a constant thickness in the area of the labial side 6, as do the other areas, as shown in FIG. 2. A blind hole 8, adapted in size to the size of the respective tooth and whose diameter and depth may be roughly 2–3 mm and roughly 4–6 mm respectively, is formed in the basal side 4 of the solid core 1 in the tooth axis. The blind hole 8 is formed with smooth walls so that no sharp edges are present and therefore tension cracks cannot form. This blind hole 8 serves, on the one hand, for mounting the solid core 1 inside an injection form for conducting the injection-molding process and, on the other hand, for fastening the finished tooth on a plastic base when producing a dental prosthesis. A transparent (amorphous) plastic that meets the requirements of DIN 13931 or ISO 3336 can be used as the material for manufacturing the tooth according to the invention. Specifically, a transparent polymer can be used. A suitable plastic material is polymethylmethacrylate (PMMA) and/or its copolymers. It is advantageous to use an impact-resistant modified PMMA. It may also be practical according to the invention if mixtures of plastics with an identical refraction index are employed. Such mixtures consist of a standard PMMA and impact-resistant modified PMMA, with a mixing ratio of 30% standard PMMA and 70% impact-resistant modified PMMA being practical. It is also possible, however, to employ a mixture of polymethyacrylmethylimide (PMMI) and a methylmethacrylate-styrene copolymer, where it is practical if 60% PMMI and 40% methylmethacrylate-styrene copolymer are present. It is also possible according to the invention for a mixture of a copolymer of methylmethacrylate and styrene with a methylmethacrylate content of more than 60% to be used.

It can also be advantageous according to the invention if an injection-moldable ceramic mass consisting of a ceramic powder such as $Al_2O_3$ or $ZrO_2$ with a plastic additive serving as a binder is used as the production material.

This injection-moldable ceramic mass is processed in an injection molding machine and the injection-molded tooth is removed as a so-called green product from the injection molding machine. The binder is removed from this green product in a binder-removal oven, that is, the plastic additive used as a binder is driven out, so that the binder is removed as completely as possible from the casting, with any change in shape being avoided if at all possible. Subsequently, there is a sintering process in a sintering oven and any required finishing work.

According to the invention, the solid core 1 and the external layers have different colorations. Thus the solid core 1 is advantageously colored dark, the translucent external layer 2 has a somewhat lighter coloration, and the outermost external layer 3 is light and translucent. It can also be practical to provide even more translucent external layers. Due to the enveloping construction of the layers 2,3 a color appearance optimally matched to natural teeth can be achieved. This of course makes color transitions without separation lines possible. Due to the formation of the blind holes 8 in the teeth according to the invention, a subsequent boring of anchoring holes is unnecessary, so that the risk of creating crack-generating sharp edges is excluded.

Specifically, a multi-component injection molding process is employed for producing the tooth according to the invention. In case a three-layer tooth is being produced, i.e., a tooth according to FIGS. 1 and 2, the core material of the solid core 1 is a first step into a first tool cavity. After that, the tool opens and the tool half with the injection-molded solid core 1 turns by 120.degree. Here a plastic material of the type used has a plastic but already form-stable consistency and has been cooled down roughly to its glass transition temperature. Upon closure of the tool, the solid core 1 moves into a second, somewhat larger cavity for injecting the external layer 2. A temperature is present here at the interface between the core and the external layer 2 that permits a fusion of the two layers. After the injection of the external layer 2 around the core, the tool opens and the movable tool half turns by an additional 120.degree., so the injection-coated solid core 1 moves into a third cavity when the tool closes. In this cavity, which corresponds to the geometry of the finished tooth, the outer layer 3 is injected on the tooth. After sufficient cooling, the tool opens and the finished tooth is ejected. The temperature conditions while injecting the external layer 3 onto the external layer 2 are the same as those in injecting the plastic layer 2 onto the solid core 1. After the finished tooth has been ejected, the movable tool half turns by an additional 120.degree. so that the tool is back in its initial position. The entire injection cycle runs completely automatically and the layers of the tooth according to the invention which are produced are the same in each cycle due to the process. The layers 1,2,3 preferably consist of the same plastic material, with these materials advantageously being colored differently. The injection of the respective successive layer is done so quickly that the contact temperature arising at the contact surface with the lower layer is higher than the softening temperature of the respective plastic.

An injection molding tool used according to the invention can be constructed such that several teeth, for instance a complete set of teeth, are injection-molded at one time.

Figure 5:
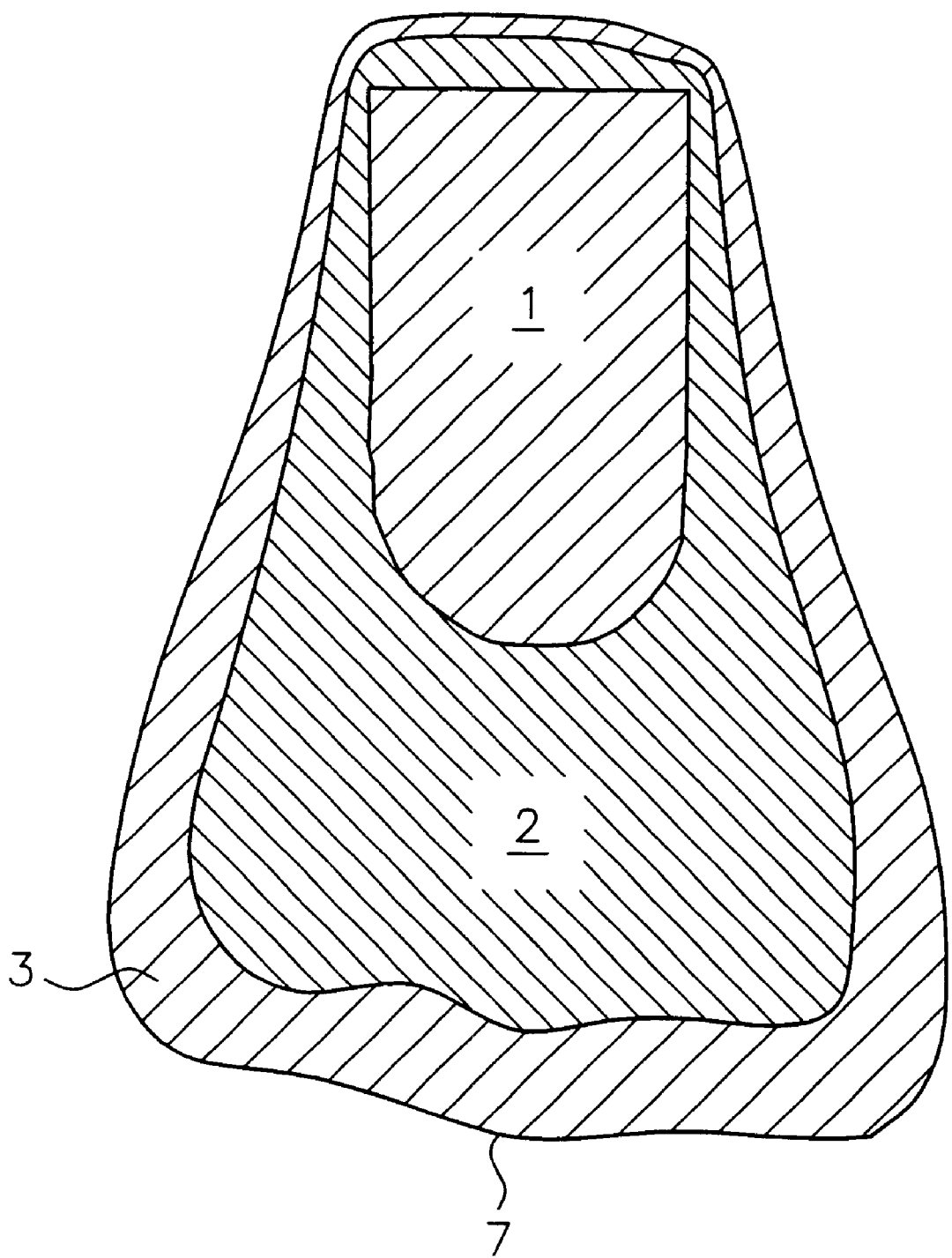
FIG. 5 an additional embodiment of a tooth according to the invention in the view of FIG. 2.

As an alternative production process to that according to the invention, it is also possible to use a multi-component injection molding process in which an appropriately stratified structure of the tooth body is achieved solely by the metering of the differently colored materials, so that only the cavity with the tooth geometry is needed. In this case, using, for example three plastification units, the components for the outermost external layer 3 and the components for the external layer 2 are metered in succession into a feeder channel of the injection mold and then, after switching over to the third plastification unit with the succeeding component for the solid core 1, all three are injected into the tool in such a manner that the mold filling takes place in expansion flux. During advancement of the melt front a part of the front material adheres to the cold mold walls and thus forms the external layer 3. The metering is to be selected such that material of this component remains in the flow front until the complete filling of the mold. Due to a temperature gradient perpendicular to the mold wall, the succeeding component behaves similarly to the first, forms the middle external layer 2 and encloses the core material 1. In case of injection from the basal side, one obtains a layer structure similar to the illustration in FIGS. 1 and 2, however, with the solid core 1 also enclosed on the basal side by the external layers 2 and 3, see FIG. 5. Due to the nature of the process, the thickness of the external layers 2 and 3 increases slightly from the basal side towards the cutting edge, which improves the appearance of the tooth. The thickness of the external layers 2 and 3 can be influenced by the choice of process parameters, such as metered amount, mass temperature, tool temperature and injection rate. The injectable ceramic mass behaves in processing on the injection molding machine in a manner corresponding to a filled plastic, so that the advantageous processes as described above can also be applied even using the injection-moldable ceramic mass.

A side tooth produced according to the invention has in principle the same succession of layers as the front tooth according to FIGS. 1 and 2, with different fundamental structures of the solid core 1 and the external layers 2 and 3, due to the form of the side tooth. In this case the occlusal side 7 takes the place of the incisal side 7 and the buccal side 6 takes the place of the labial side 6.

Figure 3:
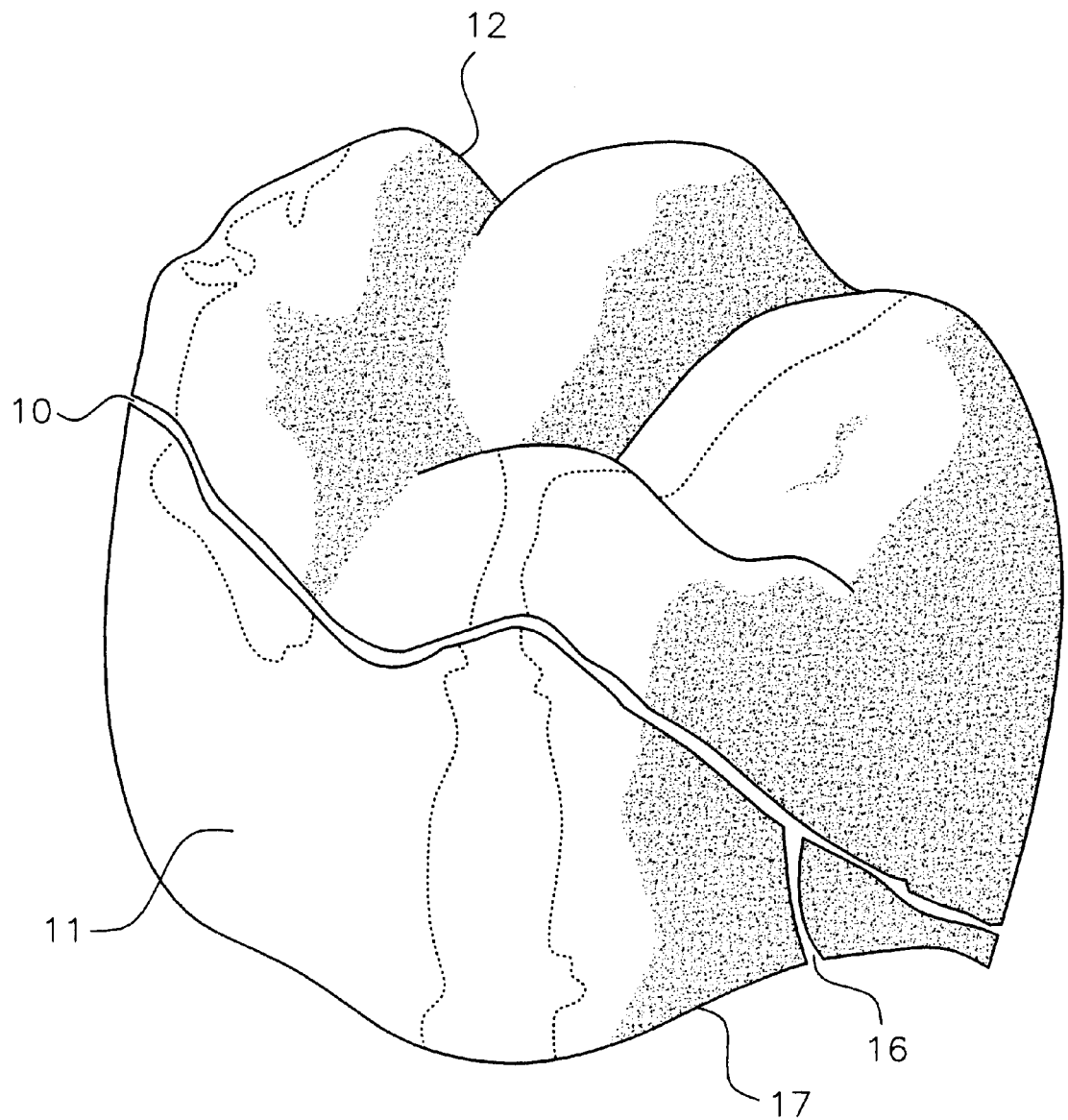
FIGS. 3 & 4 perspective views of a side tooth according to the invention.
Figure 4:
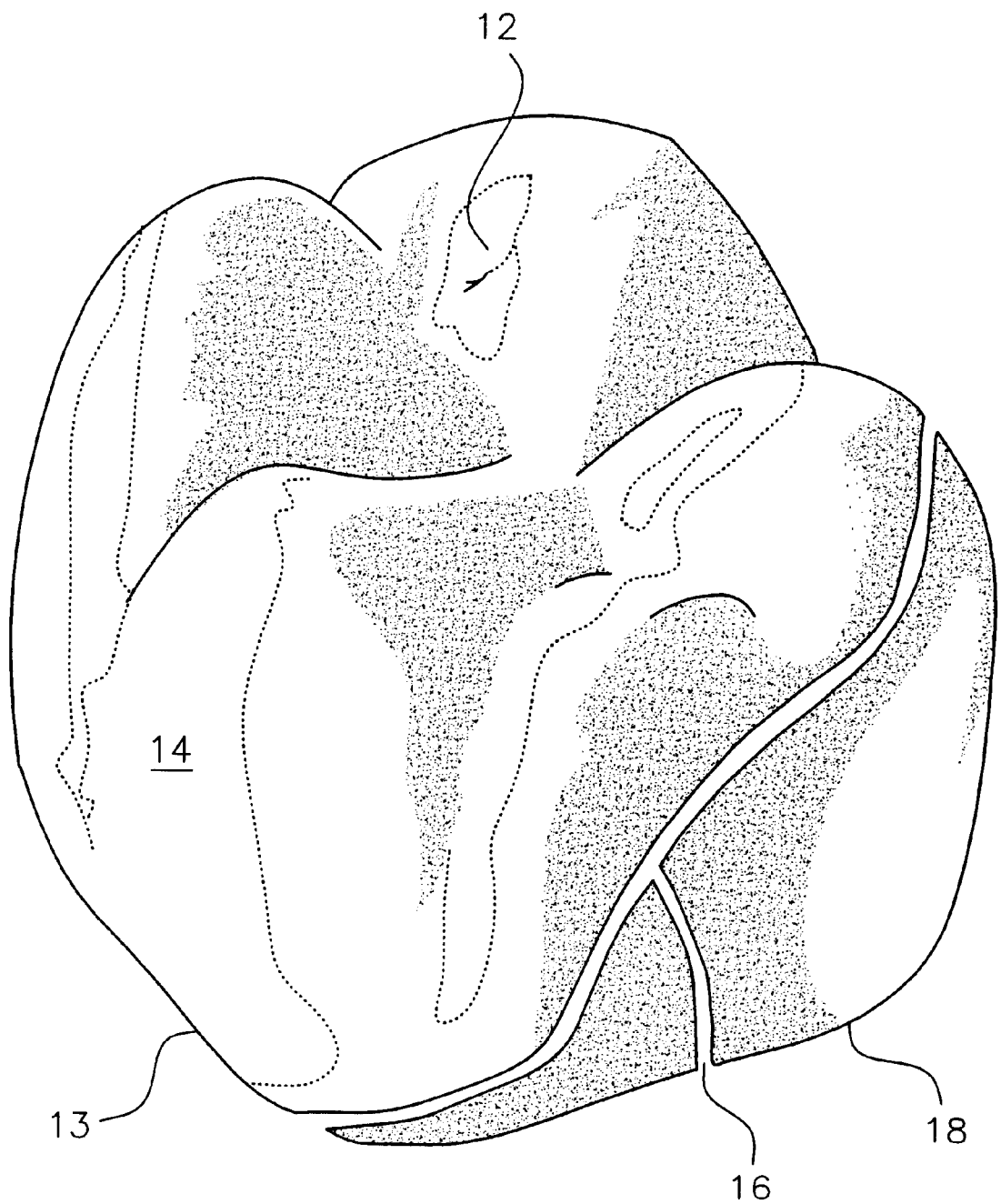

It is shown in FIGS. 3 and 4 the course of the mold mark, created during removal of the finished injection-molded tooth body from the injection mold because of the position of its separation planes, in a side tooth according to the invention. It is provided according to the invention that the mold marks run on the finished tooth body such that they are not visible in the human mouth in the inserted state. In the tooth body of a side tooth according to the invention shown from a lingual perspective in FIG. 3, it is recognizable that a lingual mold mark 10 runs in the transition between the lingual side 11 and the occlusal surface 12 of the tooth body. In FIG. 4, which shows a buccal side view of a side tooth according to the invention, it is recognizable that a buccal mold mark 13 is provided in the transition between the buccal side 14 and the base 15 of the tooth body. It is also evident from FIGS. 3 and 4 that the mold marks 16 on the two side faces 17,18 of the tooth body each runs roughly diagonally connecting the ends of the lingual mold mark 10 and the buccal mold mark 13.

In a tooth element according to the invention formed as a front tooth, the mold marks are centrally arranged on the two side surfaces of the tooth body such that they run from the base of the tooth body to the tooth's cutting edge.

Figure 6:
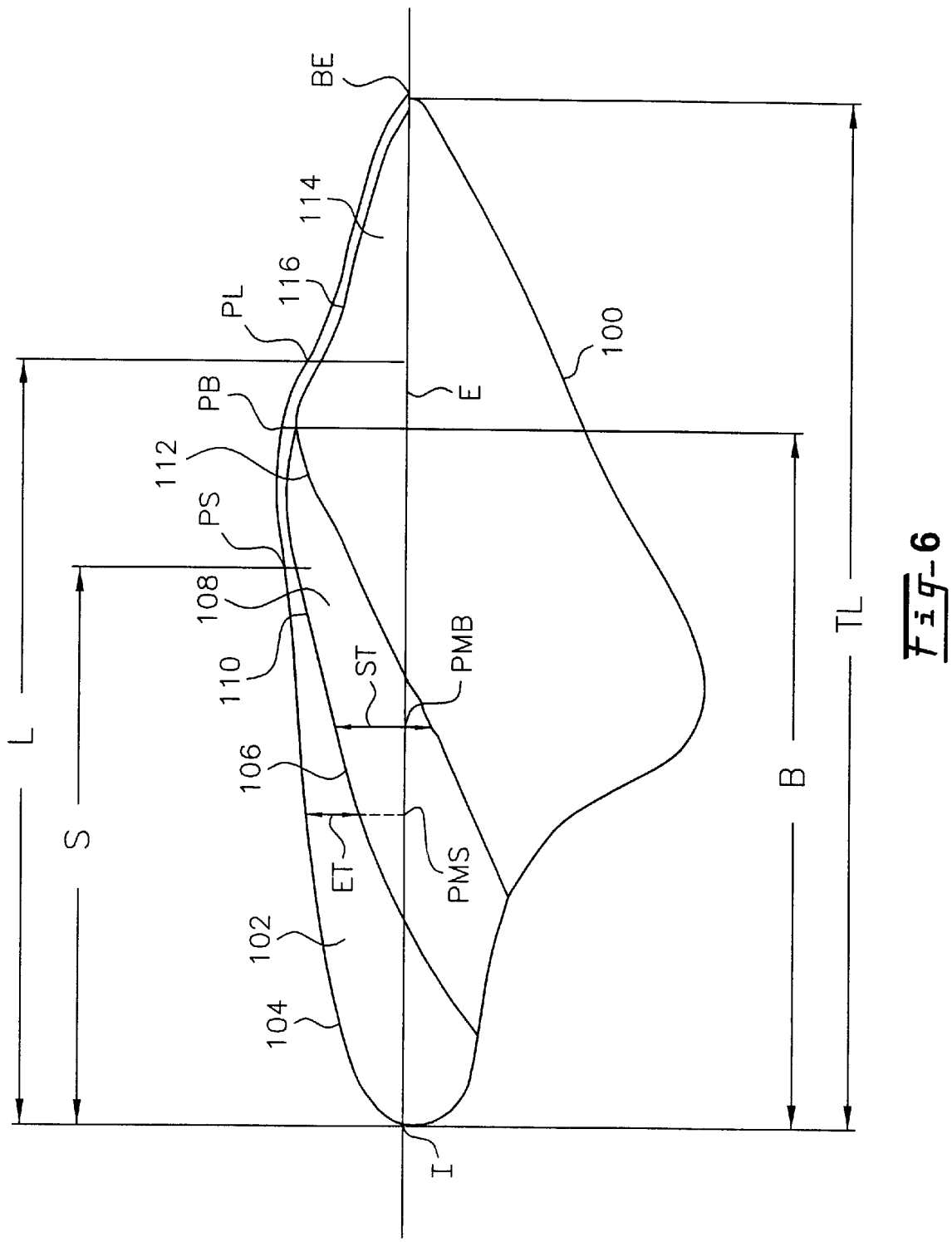
FIG. 6 is a schematic side view of a prosthetic tooth in accordance with the invention.

The invention is now described with more particular references to FIGS. 6–13. A prosthetic tooth 100 in accordance with a preferred embodiment of the invention includes enamel layer 102 having labial face 104 and shader face 106, shade layer 108 having enamel face 110 and back face 112 and back layer 114 having shader face 116 as shown in FIG. 6. The overall tooth length (TL) as used herein refers to the distance measured along the elongated central axis (E) of the tooth from the tip of the incisal edge (I) of a tooth to the point (BE) on the edge of back 114 furthest from the incisal edge (I).

Overall labial length (L) as used herein refers to the distance measured along the elongated central axis (E) of the tooth from the tip of the incisal edge (I) of a tooth to the point (PL) on the outer face of the neck of the tooth midway between the highest and the lowest points on the neck as shown in FIG. 6.

Back length (B) as used herein refers to the distance measured along the elongated central axis (E) of the tooth from the tip of the incisal edge (I) of a tooth to the end of the second back layer (PB) which is preferably about the highest point on the neck as shown in FIG. 6. The shade layer thickness (ST) at the midpoint (PMB) of the back length (B) is preferably about 0.09 inch.

Shade layer length (S) as used herein refers to the distance measured along the elongated central axis (E) of the tooth from the tip of the incisal edge (I) of a tooth to the point (PS) wherein the enamel layer changes from decreasing to constant thickness as shown in FIG. 6. The enamel thickness (ET) at the midpoint (PMS) of the shade layer length(s) is preferably about 0.031 inch.

Multiple layered teeth are provided that have a uniform thickness of enamel across a latitudinal cross section from the neck of the tooth to the center of the labial surface. This uniform enamel thickness is imaged by offsetting a copy of the labial surface of an anterior tooth and partially shaping the offset copy of the enamel surface into a curved surface to form an image of a shade layer outer surface. A shader mold part is later cut into a solid block of material, preferably metal, to provide a mold surface corresponding to the image of the shade layer outer surface.

As shown in FIGS. 6 and 6A prosthetic tooth 100 includes an enamel layer 102 having a zone Z of substantially constant enamel thickness. The enamel thickness extending normal to the central axis E of the tooth at any point, for example point 150, selected on the labial face 104 is within 0.003 inch of the thickness at any other point within 0.005 inch of the selected point. In a preferred embodiment of the invention the enamel thickness has an average thickness and said average thickness varies less than 20 percent within said zone, and said zone is circular having a diameter of at least 0.01 inch. The zone of substantially constant thickness extends preferably at least between 20 percent and 75 percent of the overall labial length of the tooth. Preferably the substantially constant enamel thickness varies less than 25 percent within any enamel zone which extends normal to the shade layer, and the zone is at least 2 mm.sup.2 more preferably at least 4 mm.sup.2 and most preferably at least 8 mm.sup.2. More preferably the substantially constant enamel thickness varies less than 20 percent within the zone. Preferably the area of the zone is substantially circular. Preferably the enamel thickness is between about 0.003 and about 0.03 inches. Preferably the enamel thickness is between about 0.08 and 0.03 inches toward the incisal end of the tooth. Preferably the enamel thickness is less than 0.003 inches toward the back end of the tooth. Preferably the tooth has a neck member. Preferably the tooth includes two overall symmetrical regions between three substantially thicker regions on the labial face of the body at the incisal end of the body between 0 and 20 percent of the overall tooth length.

Figure 11:
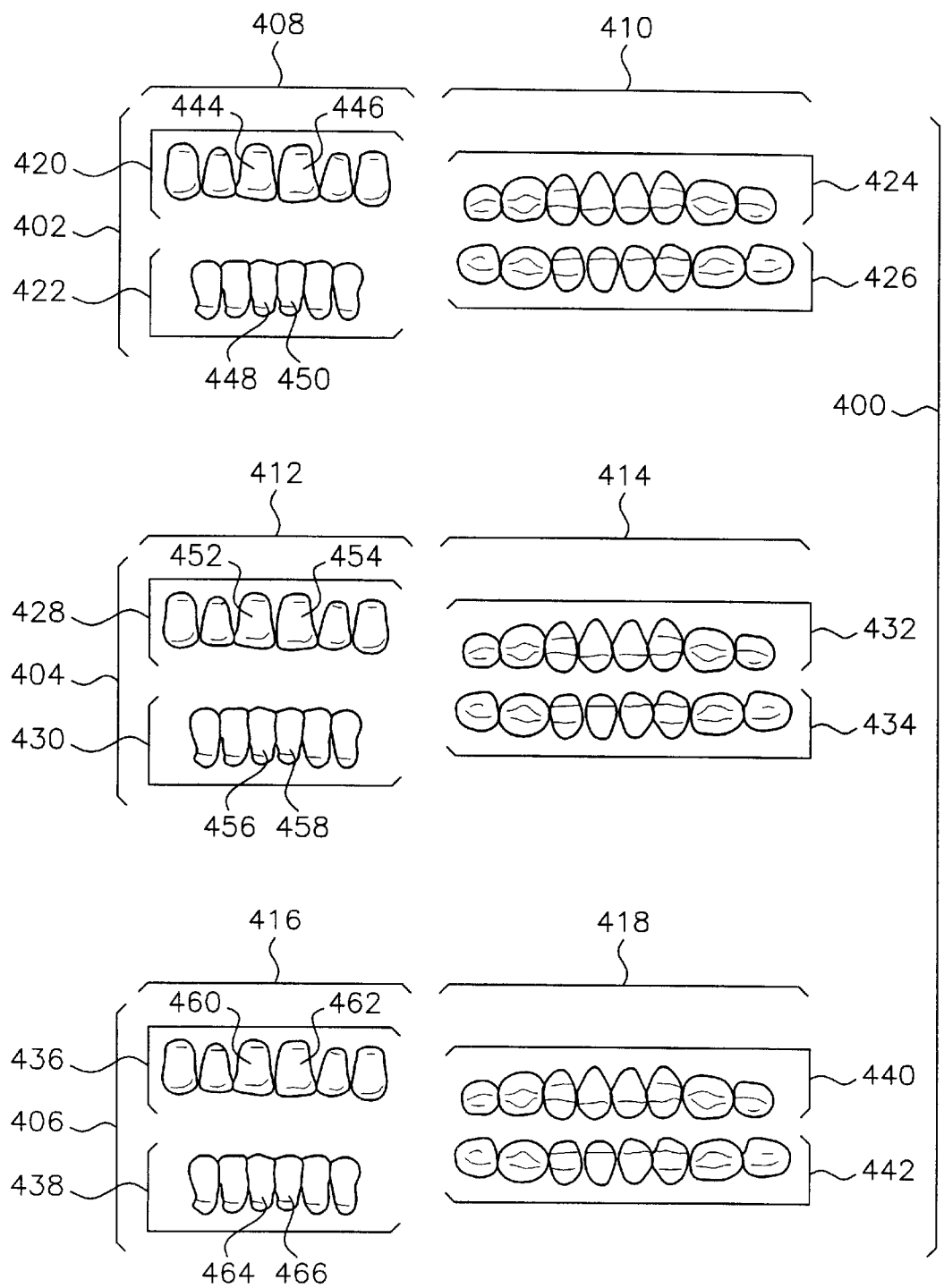
FIG. 11 is a schematic view of a family of prosthetic tooth sets in accordance with the invention.

Preferably within a family of teeth multi-layered anterior teeth are provided that have constant dimensional ratios. These dimensions are measured on longitudinal cross sections of the teeth from the family of teeth as shown in FIGS. 6 and 11.

Posterior teeth are provided in accordance with the invention that have constant dimensional ratios. All teeth within a family of such teeth exhibit similar characteristics for making a denture. Articulation of upper and lower teeth made in accordance with the invention is easier and more complete than it is for prior art teeth. Small, medium and large teeth within a family all exhibit the same articulation characteristics.

Three-dimensional tooth surface, tooth layer, and/or tooth mold part patterns are displayed on video display monitors from stored, edited and/or digitized data. The operator examines, measures and/or modifies qualities of the surface pattern such as the size and shape of the tooth and labial striations, desired for the dental mold. By visual analysis and comparison to known geometric values, e.g., length, width, thickness, for the teeth, the operator determines to add, and/or omit data via input devices, such as a keyboard. A desired three-dimensional surface pattern is thus created and displayed.

The data used for the three-dimensional surface pattern displayed is used by CAM or computer-assisted manufacture to produce a tool path program for the fabrication of the dental mold. The tool path program is used to direct and control a machine tool. The machine is preferably of multi-axes. The program will direct a milling cutter or cutters in the milling of a tooth mold from a suitable substrate, for example, steel, nickel, aluminum, ceramic, plastic or any machinable material. Steel is the preferred substrate. After the mold has been cut, the tool path program is preferably used to direct and control the application of the finish-polish to the mold. The finish-polish step improves the surface finish and results in a mold suitable for the manufacture of artificial teeth. A final hand-applied finish-polish step is optional.

Tooth molds for the manufacture of an artificial tooth requires a high degree of definition to produce the labial striations or markings on a tooth and multiple molds are needed to produce a blend of color capable of producing a natural appearance in the artificial tooth.

Imaging of enamel, shader, and back and second back mold parts is useful in accordance with a preferred embodiment of the invention to make mold parts for production of central, lateral, and canine prosthetic teeth. Size proportioning for imaged enamel, shader back and second back for different sets of teeth with a family of teeth provides proportional consistency of the teeth within the family. Specific points are selected and distances there between are maintained proportionally constant within a family of teeth. Preferably thickness dimensions are measured from the facial topography to keep consistency in the shape of the tooth and in the enamel thickness.

In accordance with a preferred embodiment of the invention a shader and second back are imaged by first determining the overall labial length (L) of the tooth. The location of the shader and second back blend starting locations PS and PB respectively are determined by multiplying the overall labial length (L) of the tooth by a different constant for each tooth set of a tooth family. The back length (B) is then broken into portions each represented by a constant for each tooth set within a tooth family. The shape and location of shader mold surface contours for central and lateral teeth and/or blend thicknesses are determined and/or developed.

Figure 7:
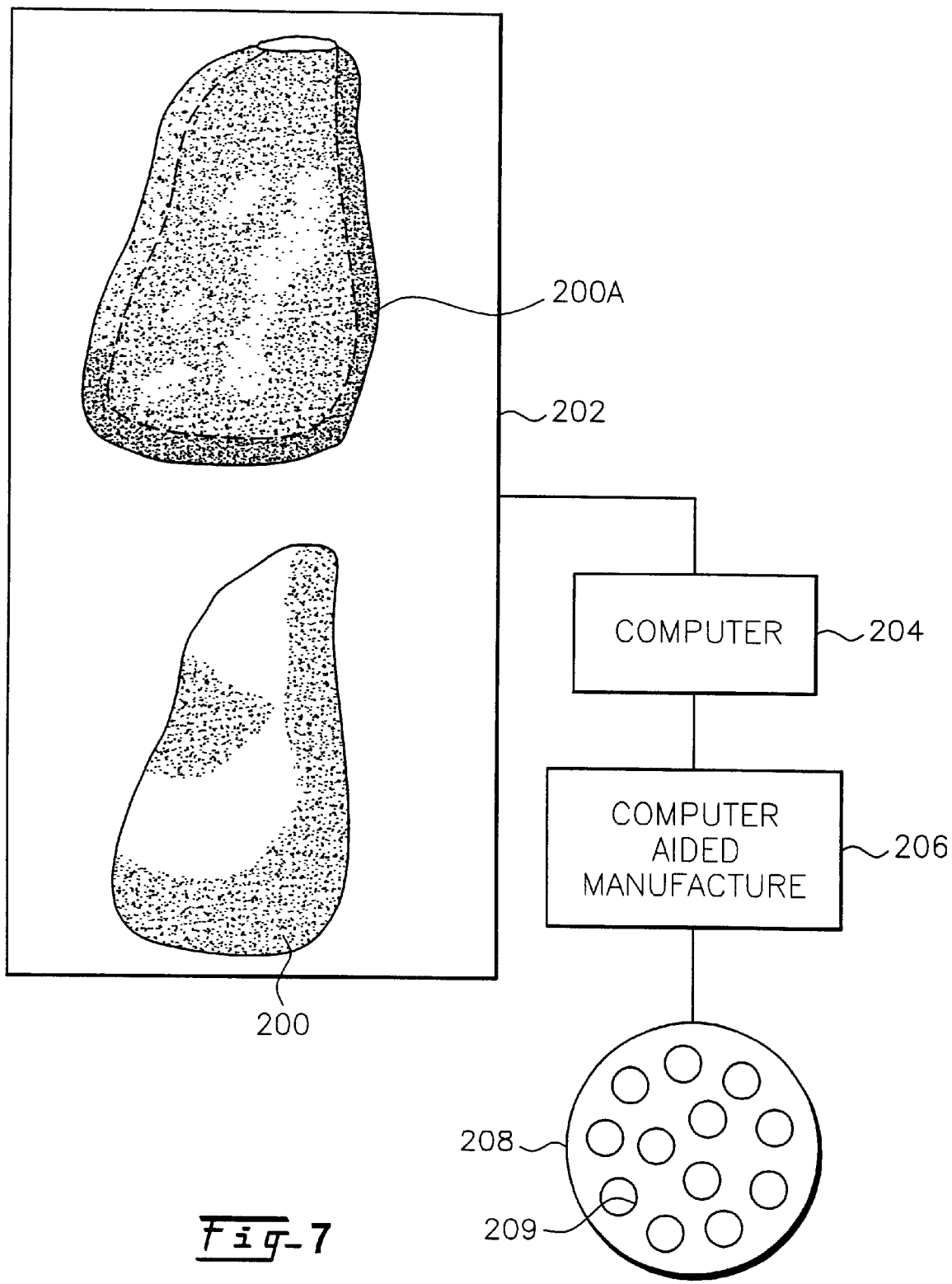
FIG. 7 is a schematic perspective view of a system displaying an enamel layer and an enamel mold part in accordance with the present invention.
Figure 8:
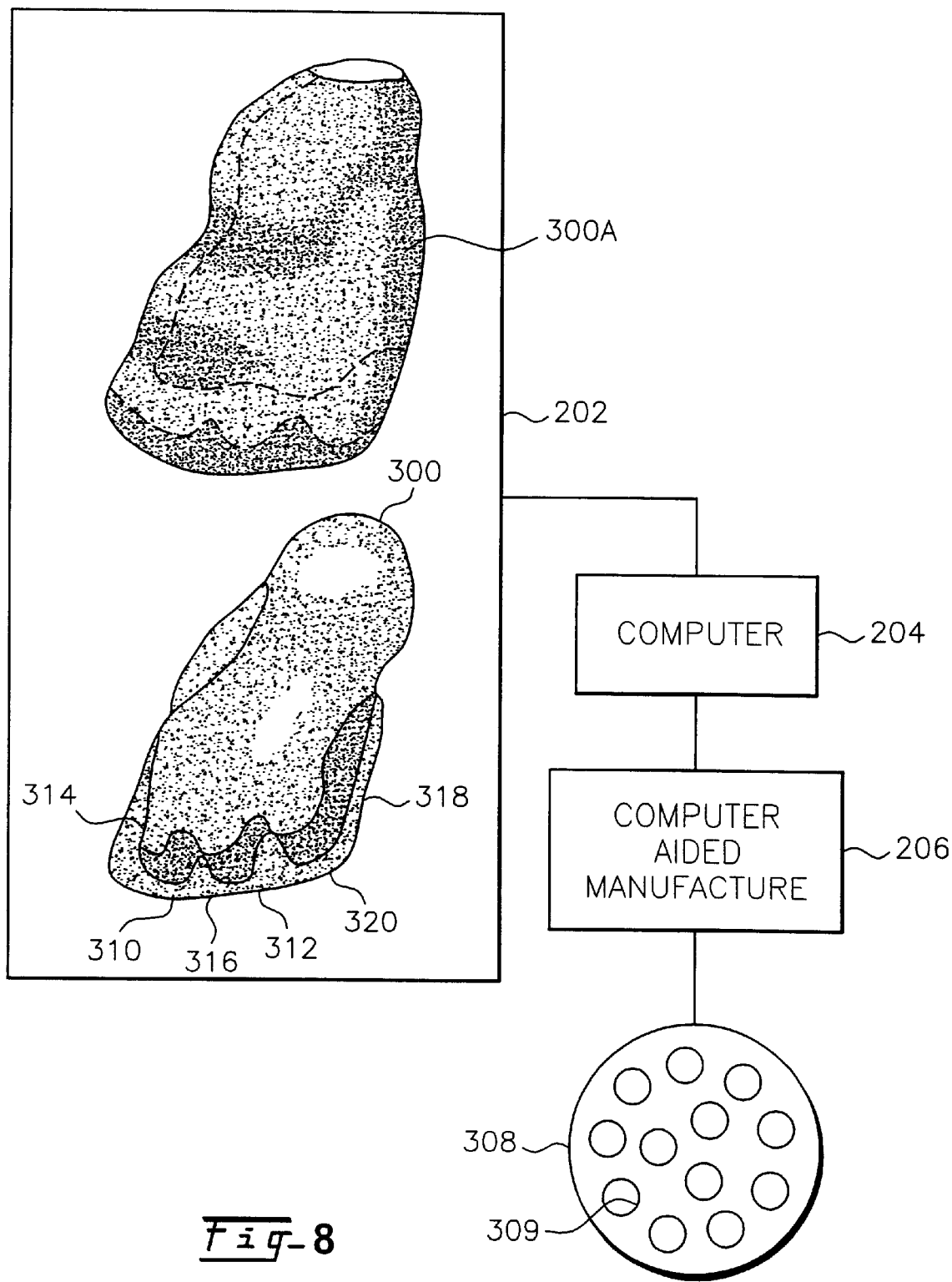
FIG. 8 is a schematic perspective view of a system displaying a shade layer and a shader mold part in accordance with the invention.
Figure 9:
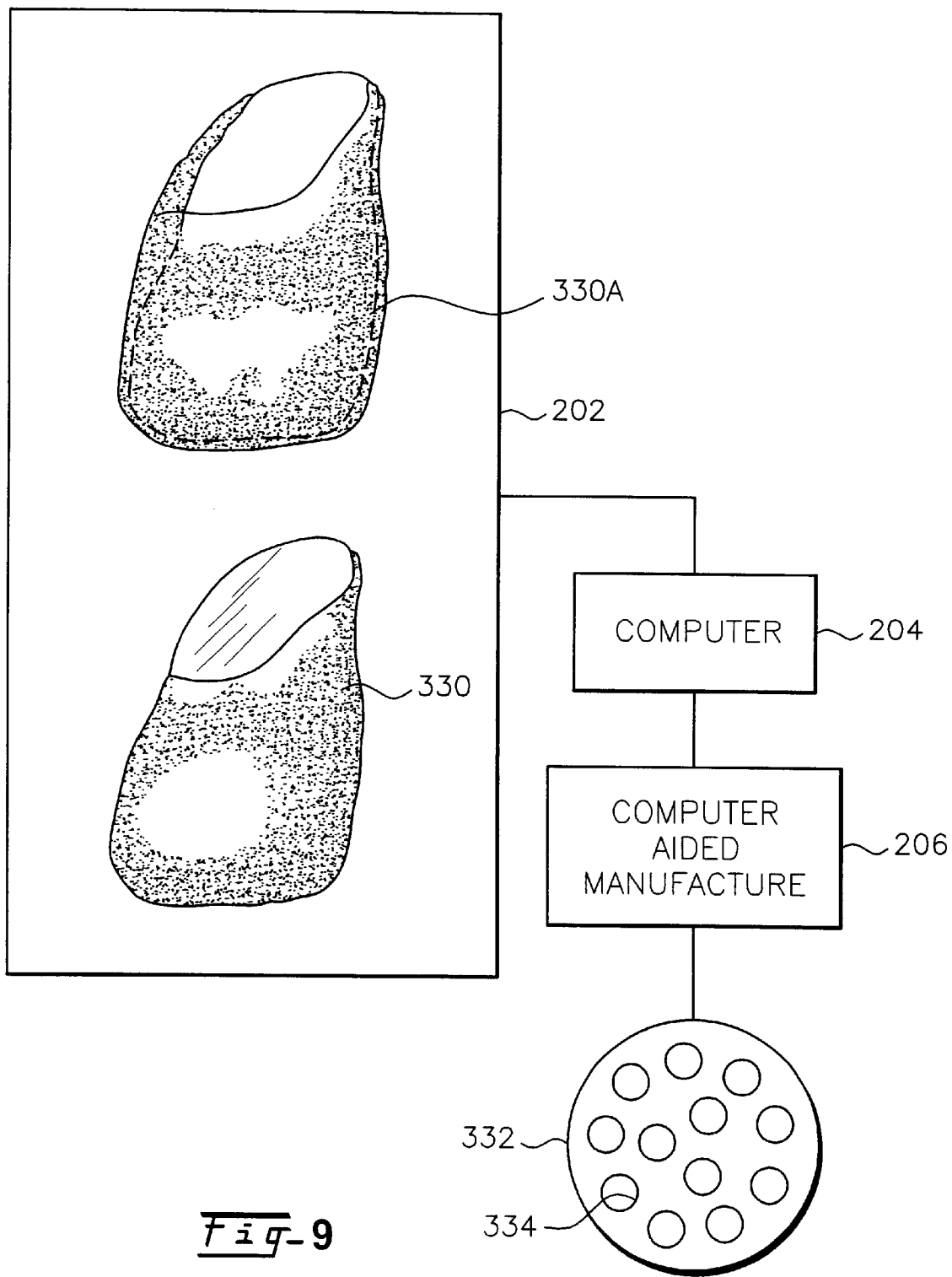
FIG. 9 is a schematic perspective view of a system displaying a second back layer and a second back mold part in accordance with the invention.
Figure 10:
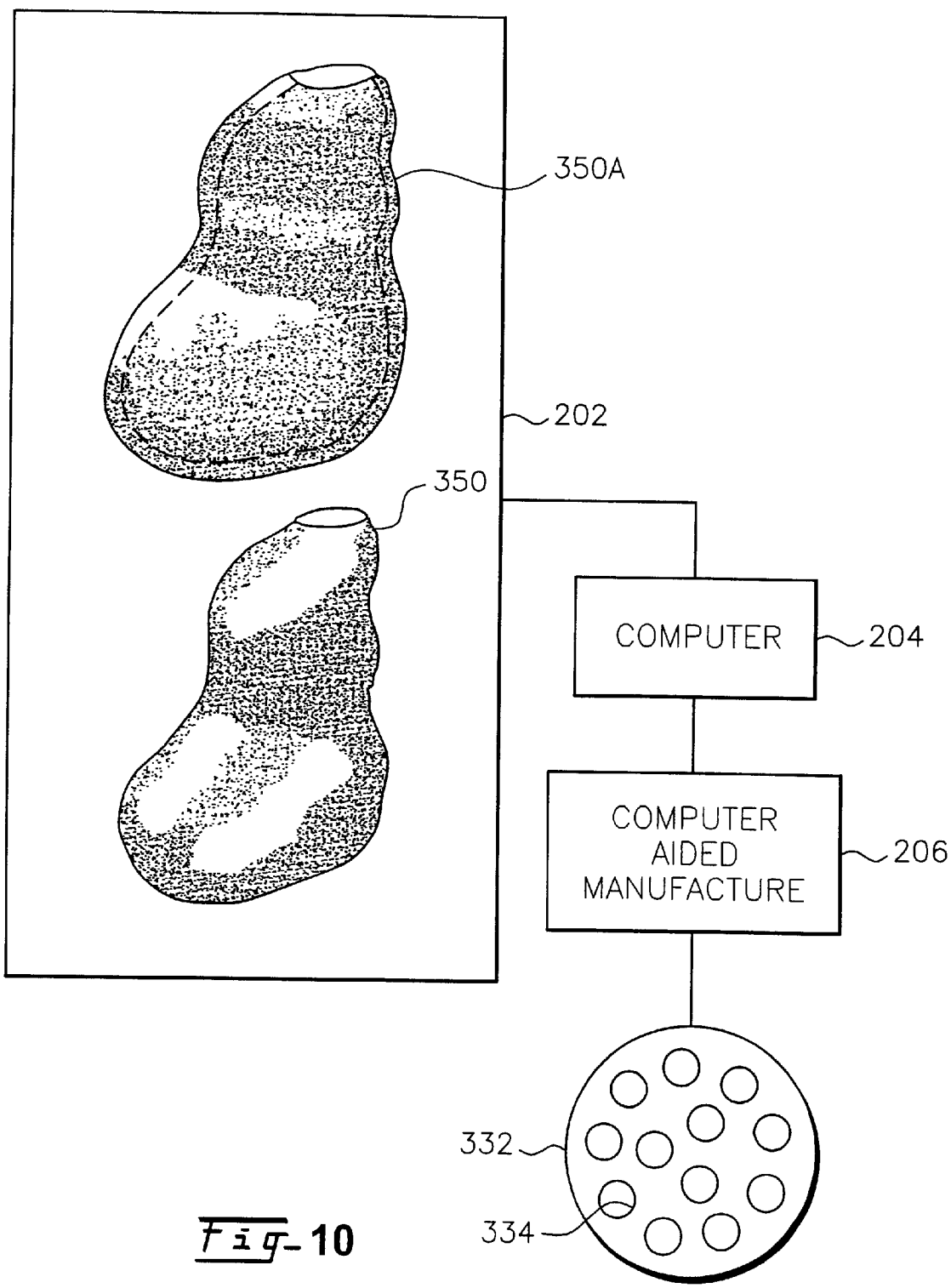
FIG. 10 is a schematic perspective view of a of a system displaying a back layer and a back mold part in accordance with the invention.

Images of an enamel mold part 200 and enamel layer 200A on display 202 are shown in FIG. 7. Images of shader mold part 300 and shade layer 300A are shown in FIG. 8 images of second back mold part 330 and second back layer 330A are shown in FIG. 4. Images of back mold part 350 and back layer 350A are shown in FIG. 10. Display 202 is connected to computer system 204. Preferably a tooth enamel mold part 208 is milled in a metal substrate by computer aided manufacture system 206. Mold parts 208, 308, 332 and 352 are cut by computer aided manufacture system 206 with multiple molding sites 209, 309, 334 and 354 as shown in FIGS. 7 through 10. Preferably a prosthetic dental tooth, such as tooth 100, having a shade layer, such as shade layer 108, corresponding to shade layer image 300 is formed in a molding site of a shader mold part, such as shader mold part 308. Each mold part is cut by computer aided manufacture system 206 with multiple molding sites therein, each of which is adapted to form a layer of a tooth corresponding to a layer image. Preferably the forming includes using a tool path program to direct machine cutting and/or finishing-polishing the tooth mold part. Preferably polymerizable acrylate material is sequentially inserted between pairs of mold parts to sequentially form a prosthetic tooth having enamel, shade, second back, and back layers. Thus, a preferred embodiment of the invention provides a prosthetic tooth including an enamel layer, a shade layer, a second back layer and a back layer as shown in FIG. 1.

Shade layer 300 has two generally symmetrical curved grooves corresponding to groove images 310 and 312 between three curved ridges corresponding to ridge images 314, 316 and 318, on the labial face of the shade layer at the incisal end of the tooth, as shown in FIG. 8. The grooves are deepest at the incisal end and extend substantially from the incisal edge to at least about 15 percent of the overall tooth length. Each groove 310 and 312 has a bottom that is substantially smooth. The sides of grooves 310 and 312 intersect the plane of the top of ridges 31, 316 and 318 at the ends of the grooves opposite to the incisal end 320. Grooves 310 and 312 extend at least about 5 percent of the lengths of shade layer 300. Preferably the tooth includes a tooth shade layer and a tooth enamel layer. Preferably the depth of each groove is from about 0.5 to 1.5 times the width of each groove. Preferably the cross section of the shader mold upper surface adjacent to the incisal edge forms a sine curve.

Figure 10A:
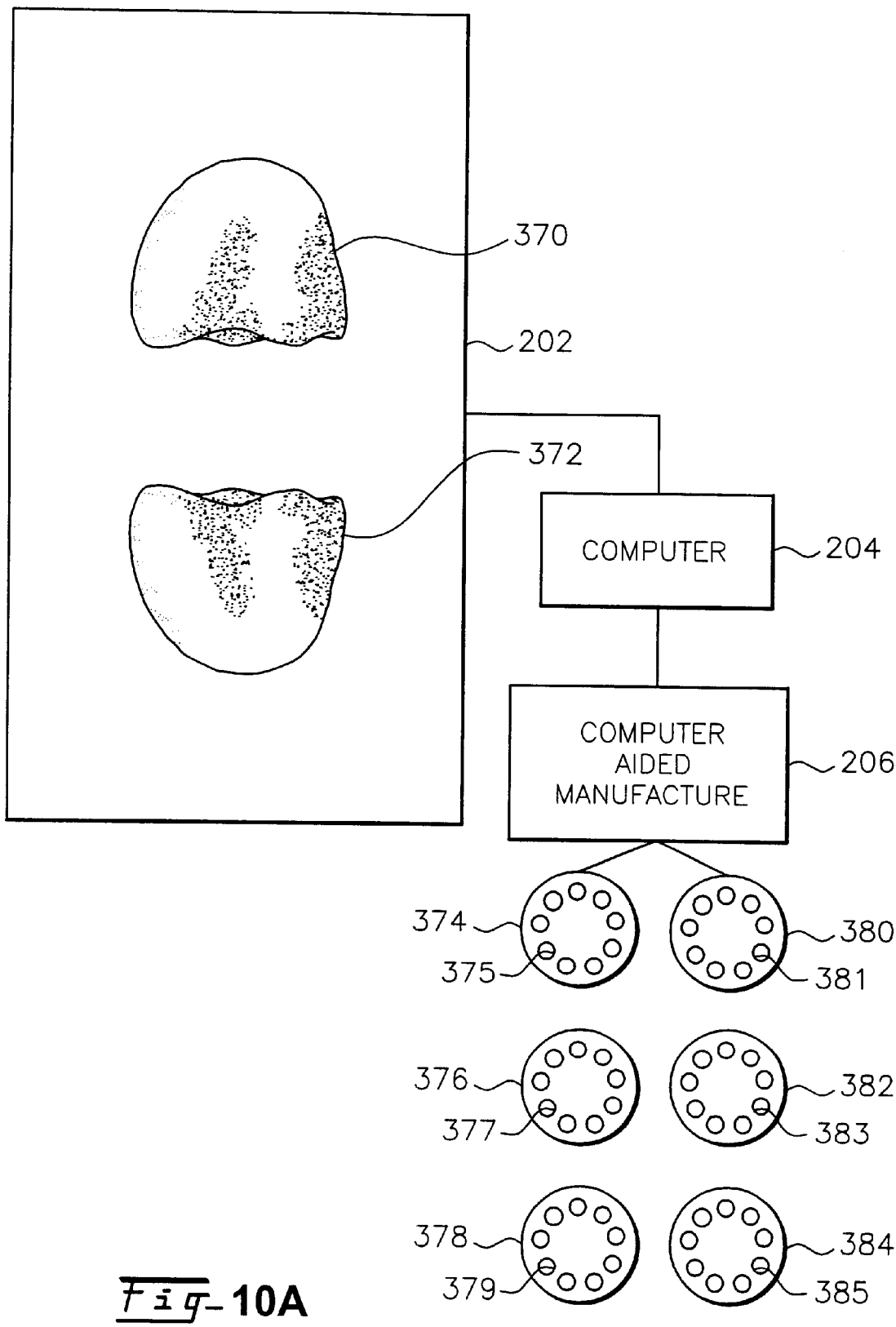
FIG. 10A is a schematic perspective view of a system displaying upper and lower molar teeth in accordance with the invention.

As shown in FIG. 10A molds for making readily articulable prosthetic teeth, are made by displaying an image of at least a portion of at least one upper tooth and at least one lower tooth. Each tooth is from the same side of the same set of teeth. Data corresponding to the image is modified whereby at least a portion of at least one is more nearly parallel to at least a portion of the other tooth image. Teeth are molded in molds made using the data. During articulation of these molded prosthetic teeth the upper and the lower molded prosthetic tooth contact along a larger proportion of each tooth surface than would be contacted without previously modifying while displaying the image of the tooth.

In accordance with a preferred embodiment of the invention is provided a method of forming a shade pattern in a tooth including imaging an outer surface for a shader mold part from a labial surface image for a face mold part, cutting a shader mold part using a tool path program, and molding a tooth having a shade pattern in a mold having the shader mold part.

In accordance with a preferred embodiment of the invention is provided a tooth family including a first tooth in a first family and a second tooth in a second family. The first tooth has a first ratio of the overall tooth length to the distance from the deepest point on the labial surface of the neck of the tooth to the incisal edge of the tooth. The second tooth has a second ratio of the overall tooth length to the distance from the deepest point on the labial surface of the neck of the tooth to the incisal edge of the tooth. The first and second ratio being substantially equal. Such prosthetic teeth are preferably provided in a set which includes a first tooth having a first outer surface and a second tooth having a second outer surface.

In a preferred embodiment of the invention as shown in FIG. 11 is provided a family of prosthetic teeth 400. Family of teeth 400 includes sets of teeth 402, 404 and 406. Set of teeth 406 includes anterior teeth 408 and posterior teeth 410. Set of teeth 404 includes anterior teeth 412 and posterior teeth 414. Set of teeth 406 includes anterior teeth 416 and posterior teeth 418. Anterior teeth 408 include upper teeth 420 and lower teeth 422. Posterior teeth 410 include upper teeth 424 and lower teeth 426. Anterior teeth 412 include upper teeth 428 and lower teeth 430. Posterior teeth 414 include upper teeth 432 and lower teeth 434. Anterior teeth 416 include upper teeth 436 and lower teeth 438. Posterior teeth 418 include upper teeth 440 and lower teeth 442. Upper anterior central teeth 444 and 446, have shapes which are mirror images of each other. Upper anterior teeth 428 include central teeth 452 and 454 which have shapes which are mirror images of each other. Lower central teeth 448 and 450 have shapes which are mirror images of each other.

Lower central teeth 456 and 458 have shapes which are mirror images of each other. Lower central teeth 464 and 466 have shapes which are mirror images of each other.

Tooth 444 in set of teeth 402 has a first overall labial length, and a first back length. Tooth 452 in set of teeth 404 has a second overall labial length, and a second back length. The ratio of the first overall labial length to the second overall labial length is substantially equal to the ratio of the first back length to the second back length. Tooth 404 has a first shader length and tooth 452 has a second shader length and the ratio of the first shader length to the first overall labial length is substantially equal to the ratio of the second shader length to the second overall labial length. Preferably this consistency of these ratio is present in corresponding molar, incisor and canine teeth of different sets within family 400. Preferably the back length is substantially equal to 94 percent of the overall labial length. Preferably the shader length is substantially equal to 68 percent of the overall labial length.

Preferably the enamel thickness of prosthetic teeth of the invention varies less than 20 percent within a circular zone having a diameter equal to the thickness. More preferably the enamel thickness varies less than 15 percent within a circular zone having a diameter equal to twice the thickness of the enamel. Most preferably the enamel thickness varies less than 25 percent within a circular zone having a diameter equal to thrice the thickness.

Preferably the enamel thickness at a selected point on the labial face between 20 percent and 75 percent of the overall labial length of the tooth is within 0.003 inch of the thickness at any other point within 0.005 inch of the selected point. Preferably the outer surface of the enamel and the interface of the enamel with the shade layer having substantially the same contours within a zone of constant enamel thickness.

Figure 12:
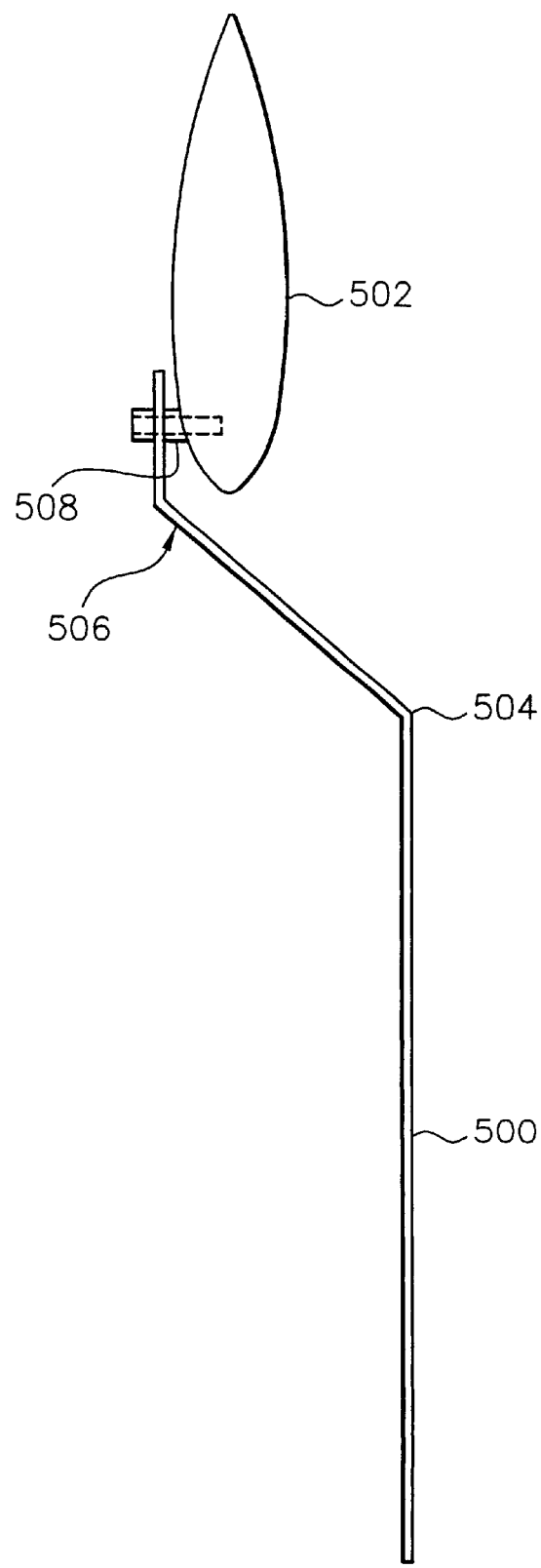
FIG. 12 is a schematic view of a shade guide member in accordance with the invention.
Figure 13:
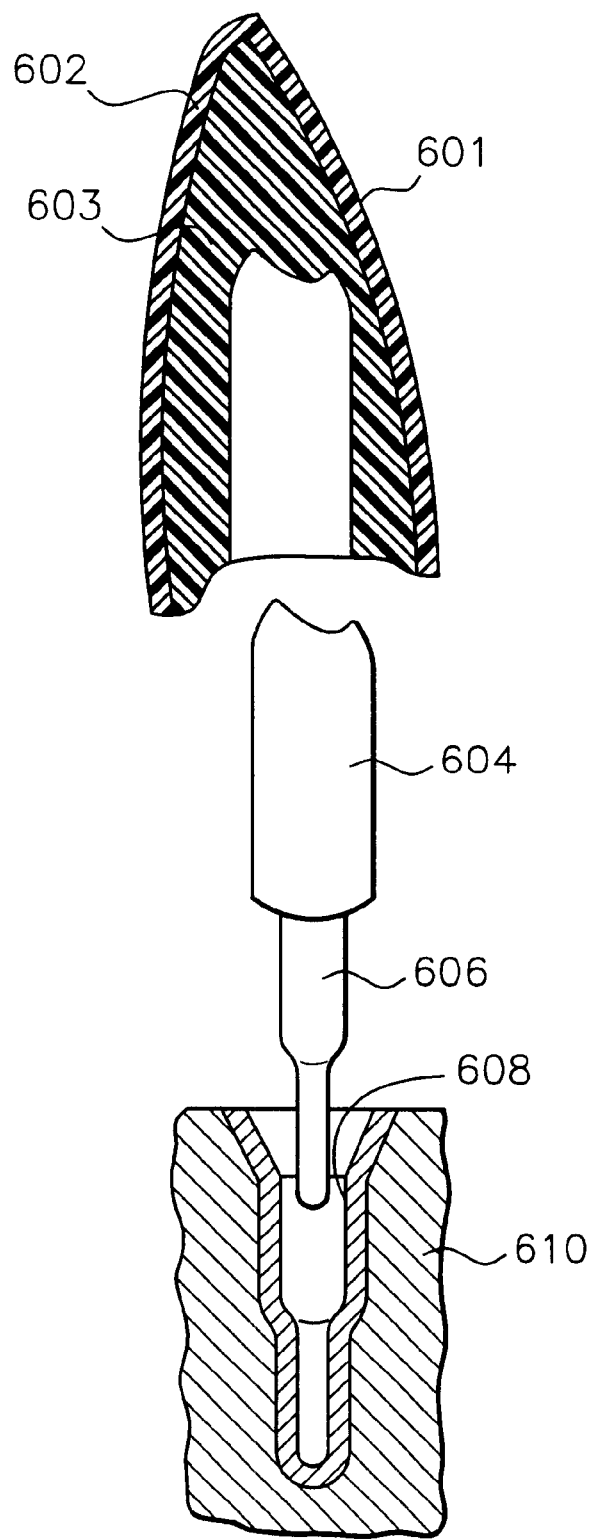
FIG. 13 is a schematic side cross sectional view of an implant crown in accordance with the invention.

Prosthetic teeth such as tooth 100 ae useful for making full and/or partial dentures, crowns, implant teeth and shade guide. FIG. 12 shows a shade guide arm 500 supporting prosthetic tooth 502. Arm 500 has bends 504 and 506. Tooth 502 is connected to arm 500 by connector 508. An implant crown 601 has an enamel layer 602 having a zone of substantially constant thickness and a shade layer 603 as shown in FIG. 8. Crown 601 is supported by core 604. Core 604 is connected to post 606. Post 606 is supported by sleeve 608. Sleeve 608 is bonded to carbon implant 610.

In accordance with a preferred embodiment of the invention digital information or data representative of a tooth enamel outer surface is prepared or retrieved from memory of a computer loaded with CAD/CAM software program, for example a Sabre 5000 CAD/CAM System, available from Gerber Systems Technology, Inc., South Windsor, Conn. The data is edited using the CAD/CAM system and two and/or three dimensional model(s) displayed on a video display monitor. The operator then offset a copy of enamel outer surface and edit the copy to design and shader outer surface. Once an acceptable surface pattern is generated. Software is used to generate a tool path program for the making of the dental mold. The data in the form of the numerical coordinates of the tool path program are collected on a memory disk and down loaded or transferred to a floppy disk.

In accordance with a preferred embodiment of the invention the floppy disk is down loaded into the hard disk drive of a milling, driving, boring and contouring machine for example a BostoMatic Model 312-1S Vertical CNC Bed Type Precision Milling, Drilling, Boring and Contouring Machine, available from Boston Digital Corporation, Milford, Mass. The tool path program is used to direct and control the machine in the fabrication of the tooth mold. The feed rate average is 6 inches per minute (range 4.5–10 inches per minute), at 30,000 rpm, for four consecutive passes with mills of decreasing size. A quarter inch end mill (Bassett) is followed by an eighth inch end mill (Bassett), followed by a sixteenth inch ball end mill (Bassett), followed by a thirty-second inch ball end mill (TSC Carbide). The tool path accuracy is 0.0002 inch and the stepover range is 0.0005–0.001 inch. The machine has four axis capability but only three axes were used in the making of the mold. The mold is cut into a block of 416 free machining stainless steel. The resultant mold is tested for surface finish qualities by subjective visual evaluation with the trained eye at 7.times. magnification comparing stone impressions from the mold with the aluminum bronze master die. The machined mold contains approximately 95% of the surface detail and finish of the master die. The mold is a coupon that is mounted into a standard aluminum mold frame for proof molding.

Finish-polishing is accomplished with the finish tool path program for example using a finish-polishing tool. The finish-polishing tool comprises a hard wood polishing stick and is used with a diamond paste; the finish-polishing step is used to get as close as possible to the complete and acceptable surface detail and finish. A final hand polishing step may be carried out using a dental handpiece (power tool), brush (synthetic bristles), and jewelers' rouge.

For making the back mold part, the digitized information from the scan of the aluminum bronze master die is processed up to readiness to be down loaded into the hard disk drive of the milling machine. For making the shader mold part, a soft Babbitt master shader die (not coated with a glarefree substance) is placed on a revolving support and processed in the same manner as the aluminum bronze master die described above. The data is processed in the same manner as for the aluminum bronze master die information up to readiness to be down loaded into the hard disk drive of the milling machine. The data is smoothed on the screen during editing to assure the fit of the shader mold part into the face mold part.

In accordance with a preferred embodiment of the invention is provided a method of repeatedly molding high definition artificial dental teeth each having a moldedenamel layer (coating). The method optionally includes scanning a model of a dental tooth. The method includes milling to make at least three mold parts. Each part is milled with a first mill by executing a first pass along a first tool path to remove material to form multiple cavities in a first metal block to make a multiple cavity mold part adapted to form multiple dental prosthetic teeth. The milling is directed by a milling-program which uses edited data. The edited data is obtained by editing reflection data using a design program. The reflection data is representative of the surface of the tooth model. The edited data is representative of the surface of the dental artificial teeth. The edited data is adapted by the milling program to direct the milling along the tool path. The mold parts are used to repeatedly mold high definition artificial dental teeth each having a moldedenamel layer (coating). When scanning of a model is used each said cavity is the negative of a portion of the model of a dental tooth to be molded in the mold. The program is produced by the steps of imaging the surface contours of the dental model and producing data readings in response to the imaging of the surface contours of the model.

In accordance with an embodiment of the invention is provided a method of making artificial dental teeth each having a molded enamel layer (coating) and high definition labial striations. Optionally a dental tooth model is provided scanned. Reflections from the tooth model are received, translated into electronic signals, which are then converted into reflection data. The reflection data is edited to add high definition labial striations using a design program to provide edited data and fabricating a metal tooth mold part. The fabricating step comprising using the edited data to direct machine milling of said tooth mold part. The milling comprising making a first pass with a first mill and making a second pass with a second mill, the first mill having a first mill end, the second mill having a second mill end, the second mill end being smaller in size than the first mill end, High definition artificial teeth are repeatedly molded using the mold part. Each tooth has a molded enamel layer (coating) and high definition labial striations. The scanning may comprise directing a laser beam onto the dental tooth model. The optional scanning step may include rotating the dental tooth model during said subjecting and receiving steps. The tooth model may be a three-dimensional wax or metal containing replica of a tooth.

The model may have a glare-free coating. The processing step may include creating an edited three-dimensional surface pattern of the tooth model from the edited data, evaluating the surface pattern of the dental tooth model, and creating a tool path program from the edited data. The evaluating step may include visual analysis of the surface pattern of the dental tooth model and comparison to known geometric values for the tooth model. The fabricating step may include using said tool path program to finish-polish the dental tooth mold part.

In accordance with a preferred embodiment of the invention is provided a method of molding artificial dental teeth each having a molded coating and labial striations. Optionally the method includes scanning a three-dimensional replica of a tooth having three-dimensional surface locations while rotating the replica. The reflections from said replica are received and translated into electronic signals, which are digitized into reflection data. The reflection data is edited to add high definition labial striations in a computer using a CAD/CAM program. A tool path program is created using the edited data. The tooth mold is fabricated using the tool path program to direct machine milling of a first, second and third metal artificial dental teeth mold parts. The milling of the first metal mold part from a first metal part includes making a first pass with a first mill and making a second pass with a second mill to mill the first metal part. The first mill has a first mill end. The second mill has a second mill end. The second mill end is smaller in size than said first mill end.

The milling of the second metal mold part from a second metal part including making a first pass with the first mill and making a second pass with the second mill to mill the second mold part.

The milling of the third metal mold part from a third metal part includes making a first pass with the first mill and making a second pass with the second mill to mill the third mold part.

The fabricating step may use the tool path program to direct machine finishing-polishing the mold part. Preferably polishing of at least one of the mold parts is directed by a finish tool path program. Preferably milling a pattern of a layer of dental prosthetic tooth to make a mold is directed by a milling program which uses edited data. The edited data is preferably provided by editing reflection data using a design program. The reflection data is representative of the surface of a tooth model. The edited data being representative of the surface of said edited dental prosthetic tooth. The data is adapted by the milling program to direct the milling.

The polishing preferably includes finish-polishing using a finish tool path and a finish-polish tool, such as a wood tool. The tool is preferably used with a paste, such as diamond paste.

In accordance with a preferred embodiment of the invention is provided a method of molding artificial dental teeth each having a molded enamel layer (coating) and labial striations. The method includes milling multiple patterns of layers of artificial teeth in first and second portions of mold making material to make first and second mold parts. The milling is directed by a milling program which uses edited data. The edited data is provided by editing reflection data using a design program. The reflection data is representative of the surface of a tooth model. The edited data is representative of the surface of the artificial tooth. The edited data is adapted by the milling program to direct the milling of said first and second mold parts. The milling of the first mold part includes executing a first pass with a first mill and executing a second pass with a second mill. The first mill has a first mill end. The second mill has a second mill end. The second mill end is smaller in size than the first mill end. The milling of the second mold part includes executing a first pass with a third mill and executing a second pass with a fourth mill. The third mill has a third mill end. The fourth mill has a fourth mill end. The third mill end is smaller in size than the fourth mill end. By repeatedly molding polymerizable material in the mold high definition artificial dental teeth are formed each having a molded polymerizable material enamel layer (coating) and labial striations.

Preferably the mold making material is readily machinable and polishable, such as steel, nickel, aluminum, ceramic or plastic.

Preferably the mold making material is steel, nickel, aluminum, ceramic or plastic. Preferably the milling includes making a second pass along the tool path with a second mill having a second mill end. The second mill end is smaller in size than the first mill end. Preferably the milling includes a making third pass along the tool path with a third mill having a third mill end. The third mill end is smaller in size than the second mill end. Preferably the milling includes making a fourth pass with a fourth mill having a fourth mill end. The fourth mill end is smaller in size than the third mill end. Preferably the mold part is a face mold part, a shader mold part, a second back mold part or a back mold part. Preferably a point of contact with a second part is provided using a surface pattern of the mold. Preferably the milling with the first mill is by executing a first pass along a second tool path to remove material to form multiple cavities in a second block to make a multiple cavity second mold part. Preferably the milling with a second mill is by making a second pass along the second tool path to remove material from the second block.

Preferred injection molding compositions are provided in the following description and examples.

In general, the novel compositions of this invention are useful for the formation, construction, and repair of dental appliances, artificial teeth, oral prosthetics, and similar articles. In addition, these compositions may be utilized for the filling of teeth, and for the surface coating thereof either to effect adhesion with oral prostheses, or to protect natural teeth from erosion, damage or decay.

In accordance with a preferred form of the present invention, hardenable dental compositions are provided which may easily and conveniently be molded by known techniques into prosthetic dental appliances possessing chemical and physical properties which are significantly improved over those of conventional prior art acrylic dental appliances. Notably, dental appliances such as, for example, prosthetic teeth produced from precursor blend compositions prepared in accordance with the invention are characterized by a grind resistance which is up to six times greater than the grind resistance of conventional plastic teeth commercially marketed at this time. Moreover, while conventional acrylic plastic teeth, upon grinding, tend to melt and curl yielding a soft plastic debris, teeth produced in accordance with the present invention yield fine, gritty debris upon grinding in generally the same fashion as do porcelain teeth.

Further, prosthetic teeth produced from the precursor blend compositions of the invention are characterized by a chemical resistance which far exceeds that of conventional acrylic plastic teeth and which approaches the chemical resistance of porcelain teeth. The solvent resistance of prosthetic teeth of the invention far surpasses that of commercially available acrylic teeth, as shown, for example, by the fact that prosthetic teeth produced from the precursor blends of the invention remain intact after three weeks of immersion in methyl methacrylate monomer, whereas conventional acrylic plastic teeth are structurally degraded by methyl methacrylate, usually in 24 hours or less.

Although possessing a superior chemical resistance, prosthetic teeth produced in accordance with the present invention have unexpectedly been found to establish an excellent chemical bond with commercial denture base systems using standard processing methods. Thus, teeth produced in accordance with the invention are superior to porcelain teeth in that they bond well to denture base, eliminating seepage between the tooth and denture base, thus avoiding foul odors and marginal staining.

In comparison to porcelain teeth, the prosthetic teeth produced in accordance with the invention are characterized as fracture resistant during denture processing and impact resistant should the denture be accidentally dropped into a porcelain sink or to the floor. The teeth described herein also give no clicking sound when occluded against each other in dentures as do porcelain teeth. In comparison with conventional acrylic teeth, the prosthetic teeth produced in accordance with the invention are characterized by outstanding monomer and solvent resistance; outstanding thermal stability, improved hardness, density, and stain resistance; and excellent hydrolytic stability. Some precursor blend compositions of the invention also provide teeth which are inherently opalescent. This characteristic enhances the appearance of the teeth, making the teeth more "natural" in appearance than conventional acrylic plastic teeth. Finally, teeth produced from the hardenable compositions of the invention exhibit excellent gloss when molded. During denture fabrication the gloss of these teeth is maintained better than that of conventional plastic teeth, due to superior chemical resistance.

The prosthetic teeth thus formed may be further characterized as having a heterogeneous microstructure. Such microstructure, which is believed to be functionally related to the superior physical characteristics of the articles formed in accordance with the practice of the invention, may be ascertained after proper preparation of a specimen of the articles through a suitable means of magnification.

Briefly stated, the hardenable dental compositions of the invention comprise a blend of components which, when combined in certain proportions and permitted to age or mature as hereinafter more fully described, produce a precursor blend that is moldable into prosthetic teeth and other dental devices. The precursor blend is formed in accordance with the invention by combining a cross-linked polymer with a monomer, a cross-linking agent for said monomer, and an optional uncross-linked polymer and/or an initiator and by allowing said combination to age or mature. The cross-linked polymer is in the form of discrete particles having average diameters ranging from about 0.001 micron to about 500 microns. Preferably, at least 50% by weight of said particles have diameters less than about 150 microns, and more preferably, less than 100 microns. If desired, a mixture of two or more different cross-linked polymers may be used. A characteristic of the cross-linked polymer is that it will be insoluble in, but will absorb or imbibe, the liquid polymerizable monomer component used in the preparation of the precursor blend. Uncross-linked polymer, if used, may be characterized as being capable of dissolving in or being dispersed by the liquid polymerizable monomer. The liquid polymerizable monomer component of the compositions of the invention is a monomer having the capacity to dissolve or disperse such uncross-linked polymer, dissolve or become miscible with the cross-linking agent, and swell the particles of cross-linked polymer used in the practice of the invention. If desired, a mixture of two or more such liquid polymerizable monomers may be used.

It has been discovered that the relative proportions of the components of the precursor blend produced in accordance with the invention are critical to the attainment of the desired properties in the final hardened or cured product produced therefrom, notably the grind resistance, wear resistance, bond strength, impact resistance, resistance to monomer and other solvents, stain resistance, thermal stability, and hydrolytic stability. Thus, it has been discovered that blends of from about 10 to about 70 weight percent of the cross-linked polymer, from about 0 to about 50 weight percent of the uncross-linked polymer, from about 20 to about 66 weight percent of polymerizable monomer, and from about 0.01 to about 27 weight percent of cross-linking agent for said monomer, together with minor amounts of initiator and in some cases activator for the initiator, provide blends which are particularly useful in the production of prosthetic teeth and denture bases characterized by properties far superior to those of conventional acrylic systems now used in the art. Prosthetic teeth possessing outstanding grind resistance, wear resistance, resistance to monomer and other solvents, stain resistance, thermal stability, and hydrolytic stability may be produced in accordance with the present invention from precursor blends including from 13 to 52 percent by weight of cross-linked polymer, from 13 to 34 weight percent of uncross-linked polymer, from 25 to 55 percent by weight of polymerizable monomer, from 7 to 22 percent by weight of cross-linking agent, and up to about 2 percent by weight of initiator.

In general, the cross-linked polymers which are useful in the practice of the invention are formed from monomers or blends of monomers together with cross-linking agents in proper proportion. The monomers suitable for use in the production of the cross-linked polymers useful in the practice of the invention, will generally comprise any of a wide variety of monomers such as, for example, acrylic and lower alkyl acrylic acid esters, N-vinyl lactams, acrylamides, acrylonitriles, styrenes, alkenes, and urethanes. Similarly, mixtures of two or more monomers may be employed to provide these cross-linked polymers.

Preferred monomeric species useful in the preparation of the cross-linked polymers of the invention include acrylic acid lower alkyl acrylic acid esters which generally conform to the structure: ##STR1## where $R_1$ is hydrogen or an alkyl group including from 1 to about 6 carbon atoms, and where $R_2$ is either (a) an alkyl or cycloalkyl group including from 1 to about 20, and preferably from 1 to about 6 carbon atoms; (b) phenyl; and (c) alkyl substituted phenyl in which the alkyl groups include from 1 to about 6 carbon atoms. Various substituents may be present on either or both of the groups $R_1$ and $R_2$. Thus, hydroxyl, amino, thiol and halogen (e.g., fluorine, chlorine, etc.) functionalities may be present, with the latter being preferred. Fluorine is an especially suitable and useful substituent.

Especially preferred examples of monomers useful in the production of the cross-linked polymers used in the practice of the invention include methyl-, ethyl-, isopropyl-, tert-butyloctyl-, dodecyl-, cyclohexyl-, chloromethyl-, tetrachloroethyl-, perfluorooctyl-, hydroxyethyl-, hydroxypropyl-, hydroxybutyl-, 3-hydroxyphenyl-, 4-hydroxyphenyl-, aminoethyl-, aminophenyl-, and thiophenyl-, acrylate, methacrylate, ethacrylate, propacrylate, butacrylate and chloromethacrylate, as well as the homologous mono-acrylic acid esters of bisphenol-A, dihydroxydiphenyl sulfone, dihydroxydiphenyl ether, dihydroxybiphenyl, dihydroxydiphenyl sulfoxide, and 2,2 bis(4-hydroxy-2,3,5,6-tetrafluorophenyl)propane. Other suitable species will be apparent to those skilled in the art. If desired, mixtures of two or more different monomers may be used to provide the cross-linked polymers useful in the practice of the invention.

The cross-linking agents which are useful in the production of the cross-linked polymer component of the invention comprise a wide variety of di- or polyfunctional moieties which are capable of cross-linking monomer species. In general, the reactive functionalities which serve as active sites for such cross-linking are ethylenic functions, but other reactive and effective cross-linking functions are similarly useful as will be hereinafter described. The use of cross-linking agents in the formulation of polymers is well known to those skilled in the art, who similarly recognize that it is necessary for such agents to have at least two reactive functionalities.

Suitable cross-linking agents may be selected from numerous families of polyfunctional monomers such as acrylic and lower alkyl acrylic acid diesters, acrylic and lower alkyl acrylic acid esters formed from alcohols, which alcohols have a second reactive function, urethane diacrylates and dimethacrylates, polyvinylic compounds, divinyl aromatic compounds and others, as will be apparent to those skilled in the art.

Preferably, the cross-linking agents comprise esters of unsaturated acids, e.g., acrylic, methacrylic, ethacrylic, propacrylic, butacrylic, etc., maleic, fumaric, citraconic, mesaconic, itaconic, malonic, or aconitic, etc., acids. Other unsaturated acids will be readily apparent to those skilled in the art. These acids are preferably reacted with either unsaturated or polyhydroxylic alcohols to form esters which are effective polyfunctional cross-linking agents useful in the formulation of the cross-linked polymers of the invention. In general, these alcohols have one or more hydroxylic functionality and have from 2 to about 30 carbon atoms. Thus, useful alcohols include allyl, methallyl, crotyl, vinyl, butenyl, isobutenyl and similar unsaturated alcohols as well as polyols such as ethylene glycol, propylene glycol, butylene glycol, diethylene glycol, triethylene glycol, tetraethylene glycol, pentaethylene glycol, glycerol, 1,3,3-trimethylolpropane, pentaerythritol, dihydroxyphenol, and alkylidene bisphenols such as bisphenol-A, 1,1-bis(4-hydroxyphenyl)methane, 4,4'-dihydroxybiphenyl, 4,4'-dihydroxydiphenyl sulfone, dihydroxydiphenyl ether, dihydroxydiphenyl sulfoxide, resorcinol, hydroquinone, etc.

Cross-linking agents preferred for the practice of the invention include the esters of a mono- or dibasic unsaturated acid with an unsaturated monohydroxylic alcohol such as allyl acrylate, allyl methacrylate, vinyl acrylate (methacrylate and $C_1$ to $C_{20}$ homologs), dimethallyl fumarate, N-allyl acrylamide, crotyl acrylate, allyl crotonate, allyl cinnamate, diallyl maleate, etc. Other preferred species are the di-, tri-, and higher esters of polyhydroxylic alcohols such as ethylene "glycol" diacrylate (dimethacrylate and $C_2$ -$C_{40}$ homologs), trimethylolpropane trimethacrylate, and the diacrylate and dimethacrylate esters of bisphenol-A as well as acrylate and alkyl acrylate esters which correspond to the general formula##STR2## wherein $R_3$ and $R_4$ may be the same or different and are hydrogen or alkyl groups containing from 1 to about 6 carbon atoms and n is a whole number from 1 to about 10. Alternatively, the cross-linking agent may conform to the formula##STR3## where $R_5$ and $R_6$ may be the same or different and are hydrogen or alkyl groups containing from 1 to about 6 carbon atoms and A is an aromatic moiety selected from the group consisting of (a) biphenyl, diphenyl alkylidene having from 1 to about 6 carbon atoms in the alkylidene portion thereof, diphenyl sulfone, diphenyl sulfoxide, diphenyl ether, and diphenyl sulfide; (b) the diglycidyl derivatives of group (a); and (c) the diurethane derivatives of either group (a) or group (b). In addition, the cross-linking agent may be of a glycidyl acrylate or allyl acrylate, divinyl (trivinyl or higher homologs) benzene, substituted divinyl benzenes, and analogous compounds. Furthermore, mixtures of two or more cross-linking agents are useful in the practice of the invention.

Compounds such as bis-GMA and the urethane diacrylate formed by reacting hydroxyethyl methacrylate with 2,2,4-trimethylhexyl-1,6-diisocyanate are especially useful, as are diallyl maleate, ethylene "glycol" dimethacrylate, trimethylolpropane trimethacrylate and the dimethacrylate ester of bisphenol-A.

The cross-linked polymers are produced by polymerizing a mixture of the monomer or monomers and cross-linking agent or agents described above. The amount of cross-linking agent employed in the production of the cross-linked polymers used in the practice of the invention is a critical factor. It has been found that the capacity of particles of polymers so produced to swell with or to imbibe the monomer component to form the precursor blend of the invention, is directly related to the amount of cross-linking agent used in the production of such cross-linked polymers.

The physiochemical properties of the cross-linked polymers useful in the practice of the invention determine the relative proportions of monomer and cross-linking agent used to formulate said suitable cross-linked polymers. Such cross-linked polymers must be sufficiently well cross-linked as to maintain substantially their structural identify when exposed to the monomer component of the precursor blend of the invention. At the same time, they must not be so thoroughly cross-linked as to be incapable of swelling with or imbibing the monomer component. Thus, it is convenient to describe the proportion of cross-linking agent by what it does rather than by what it is. In view of the fact that the cross-linked polymers are utilized in finely particulate form, as will be more fully explained, it is convenient to define the minimum amount of cross-linking agent used therein as being that amount which is sufficient to cause the particulate cross-linked polymer not to lose its particulate discreteness upon exposure to the monomer component of the invention. Similarly, the maximum amount of cross-linking agent used therein is that amount beyond which the resulting cross-linked polymer particles are unable to swell with or further imbibe a significant portion of monomer component upon exposure thereto. In this regard, a quantity of cross-linked polymer particles would be said to swell with or imbibe a significant portion of monomer component if it swelled with or has imbibed at least 10% of its own weight of monomer component. Preferably, an amount of cross-linking agent is used to provide a cross-linked polymer having the capacity to imbibe from about 10 to about 500 percent of its own weight of monomer component.

It will be clear to those skilled in the art that the minimum and maximum values for the proportions of cross-linking agents suitable for inclusion in the cross-linked polymers of this invention will vary depending upon the chemical identity of the component monomers and cross-linking agents. In general, however, the cross-linking agents may comprise from as low as about 0.01% to as high as about 30%, and preferably from about 0.2% to about 10% by weight of the resulting cross-linked polymer. For any monomer cross-linking agent system, it is well within the routine knowledge of those skilled in the art to ascertain the optimum proportion of cross-linking agent in view of the requirements set forth above.

The production of the cross-linked polymers useful in the practice of this invention from monomers and cross-linking agents may be performed by any of the many processes known to those skilled in the art. Thus, the polymers may be formed by heating a mixture of the components to a temperature sufficient to cause polymerization, either with or without the addition of initiators. For this purpose, peroxy type initiators such as benzoyl peroxide, dicumyl peroxide and other materials familiar to those skilled in the art may be employed, and the use of activators may be advantageous in some formulations. Alternatively, the cross-linked polymers of the invention may be formed from the constituents by photochemical or radiant initiation utilizing light orhigh energy radiation. For photochemical initiation, photochemical sensitizers or energy transfer compounds may be employed to enhance the overall polymerization efficiency in manners well known to those skilled in the art.

The polymerization of the cross-linked polymers may be accomplished in a wide variety of ways, all of which are known to those skilled in the art. Thus, they may be formed by suspension polymerization as taught in U.S. Pat. No. 2,673,194 to Grim, emulsion polymerization, block polymerization or any other useful and convenient process. Since, as will be more fully described herein, it is desirable to have the cross-linked polymer available in the form of finely particulated granules or beads, suspension polymerization is especially convenient. Blocks of bulk-formed polymer may be crushed to yield a useful product, however. The size of the particles of cross-linked polymer is of significance to the invention. As indicated, it is desirable that the cross-linked polymer be in the form of small, discrete particles or beads. The average particle size should be from about 0.001 micron to about 500 microns. It is preferred that at least 50% by weight of the particles have diameters below 150 microns and more preferably below 100 microns.

In addition to the cross-linked polymers described above, the polymer component of the precursor blend may comprise an uncross-linked polymer. Such uncross-linked polymer is formed from any of the monofunctional monomer species which have been disclosed above as being useful for the preparation of the cross-linked polymers used in the practice of the invention. Thus, monomer species conforming to Formula I above, the acrylic and $C_1$ to $C_6$ lower alkyl acrylic esters of aliphatic alcohols or phenols having from 1 to about 20 carbon atoms, or mixtures thereof, are suitable as is vinylidene fluoride. Polymeric methyl methacrylate and methyl acrylate are preferred. While moieties conforming to Formula I above are most preferred, each and any of the other materials disclosed as being monofunctional monomers suitable for inclusion in the cross-linked polymer are also suitable materials for use in formulation of the uncross-linked polymers. Mixtures of monomers are also quite useful. The uncross-linked polymers may be formed from the monomers through any of the polymerization procedures known to those skilled in the art. Thus, thermal or photochemical polymerization, either with or without initiators, sensitizers, activators, or chain transfer agents, may be employed. Similarly, either bulk or suspension polymerization may be utilized. Preferably, the uncross-linked polymers should be characterized as having average molecular weights of from about 100,000 to about 2,000,000 g/mole, and especially of from about 500,000 to about 900,000 g/mole. While the polymers are used in particulate form, they differ from the cross-linked polymers in that, unlike the cross-linked polymers, the uncross-linked polymers do not have a critical particle size distribution. Thus, polymer particles or beads of any conveniently small size, such as about 500 microns, may be utilized. Smaller sizes are preferred since they imbibe monomers and will dissolve therein more readily, but larger sizes may be used as well.

The uncross-linked polymers used in the practice of the present invention are quite distinct from the cross-linked polymers. The cross-linked polymers have been defined as being capable of swelling with or imbibing the monomer component of the precursor blend of the invention, and as being of a physical and physiochemical structure so as not to lose their discrete particulate identity upon such swelling. This physical definition has, similarly, been related to the proportion of cross-linking agent included therein. By comparison, the particles of uncross-linked polymer do not retain their particulate discreteness when exposed to the monomer component, but are dissolved therein if sufficient time and monomer component are provided.

The polymerizable monomers suitable for use in the formulation of the precursor blend of the invention may comprise any of a wide variety of monomers. Thus, acrylic and lower alkyl acrylic acid esters, N-vinyl lactams, acrylamides, acrylonitriles, styrenes, alkenes, urethane acrylate or methacrylate, and other monomeric species may be employed in the practice of the invention.

Preferred monomeric species are acrylic and lower alkyl acrylic acid esters which may be seen generally to conform to Formula I, above. Especially preferred examples of polymerizable monomers useful in the practice of the invention include methyl-, ethyl-, isopropyl-, t-butyl-, octyl-, dodecyl-, cyclohexyl-, chloromethyl-, tetrachloroethyl-, perfluorooctyl-, hydroxyethyl-, hydroxypropyl-, hydroxybutyl-, 3-hydroxyphenyl-, 4-hydroxyphenyl-, aminoethyl-, aminophenyl-, and thiophenyl-, acrylate, methacrylate, ethacrylate, propacrylate, butacrylate and chloromethacrylate, as well as the homologous monoacrylic acid esters of bisphenol-A, dihydroxydiphenyl sulfone, dihydroxydiphenyl ether, dihydroxybiphenyl, dihydroxydiphenyl sulfoxide, and 2,2-bis(4-hydroxy-2,3,5,6-tetrafluorophenyl)propane. Other suitable species will be apparent to those skilled in the art who will further recognize that mixtures of two or more different polymerizable monomers may be used.

As noted above, the polymerizable monomer components of the precursor blends of the invention are generally liquid at room temperature and have the capacity to dissolve or disperse the uncross-linked polymers and to swell or be imbibed by the cross-linked polymers which further comprise the precursor blend. Furthermore, the polymerizable monomers are capable of being cross-linked by the cross-linking agents as will be described below.

The cross-linking agents for the polymerizable monomers useful in the practice of the invention comprise a wide variety of di- or polyfunctional moieties which are capable of cross-linking monomeric species. In general, the reactive functionalities which serve as active sites for this cross-linking are ethylenic functions, but other reactive cross-linking functions are similarly useful. The use of cross-linking agents in the formulation and elaboration of polymers is well known to those skilled in the art, who will appreciate that it is necessary for such agents to have at least two reactive functionalities. Suitable cross-linking agents may be selected from numerous families of polyfunctional monomers such as acrylic and lower alkyl acrylic acid diesters, acrylic and lower alkyl acrylic acid esters formed from alcohols which alcohols have a second reactive function, urethane diacrylates and dimethacrylates, polyvinylic compounds, divinyl aromatic compounds and others as will be apparent to those skilled in the art.

Preferably, the cross-linking agents for the polymerizable monomers comprise esters of unsaturated acids, e.g., acrylic, methacrylic, ethacrylic, propacrylic, butacrylic, etc., maleic, fumaric, citraconic, mesaconic, itaconic, malonic, or aconitic, etc., acids. Other unsaturated acids will be readily apparent to those skilled in the art. These acids are preferably reacted with either unsaturated or polyhydroxylic alcohols to form esters which are effective polyfunctional cross-linking agents for the monomeric species useful in the practice of the invention. Thus, useful alcohols include allyl, methallyl, crotyl, vinyl, butenyl, isobutenyl and similar unsaturated alcohols as well as polyols such as ethylene glycol, propylene glycol, butylene glycol, diethylene glycol, triethylene glycol, tetraethylene glycol, pentaethylene glycol, glycerol, trimethylolpropane, pentaerythritol, dihydroxyphenol, alkylidene bisphenols such as bisphenol-A; 1,1-bis(4-hydroxyphenyl)methane; 4,4'-dihydroxybiphenyl; 4,4'-dihydroxydiphenyl sulfone; dihydroxydiphenyl ester; dihydroxydiphenyl sulfoxide; resorcinol; hydroquinone; etc.

The preferred cross-linking agents used in the practice of the invention include the esters of a monomeric dibasic unsaturated acid with an unsaturated mono-hydroxylic alcohol such as allyl acrylate, allyl methacrylate, vinyl acrylate (methacrylate and homologs), dimethallyl fumarate, N-allyl acrylamide, crotyl acrylate, allyl crotonate, allyl cinnamate, diallyl maleate, etc. Other preferred species are the di-, tri-, and higher esters of polyhydroxylic alcohols such as ethylene "glycol" diacrylate (dimethacrylate and $C_2$-$C_6$ homologs), trimethylolpropane trimethacrylate, and the dimethacrylate ester of bisphenol-A as well as other acrylate and alkyl acrylate esters corresponding to Formula II, above. Alternatively, the cross-linking agent may conform to Formula III, above. In addition, the cross-linking agent for the polymerizable monomers may be a glycidyl acrylate or allyl acrylate, divinyl (trivinyl or higher homologs) benzene, substituted divinyl benzenes, or analogous compounds. Furthermore, mixtures of cross-linking agents are useful in the practice of the invention.

Compounds such as bis-GMA and the urethane dimethacrylate formed from the reaction of hydroxyethyl methacrylate or acrylate with 2,2,4-trimethylhexyl-1,6-diisocyanate (hereinafter referred to as "urethane dimethacrylate" or "diacrylate" are especially useful, as are ethylene "glycol" dimethylacrylate, trimethylolpropane trimethacrylate and the dimethacrylate ester of bisphenol-A. The corresponding acrylates are similarly useful as is diallyl maleate.

In addition to the components described above, (i.e., cross-linked polymer, uncross-linked polymer, polymerizable monomer and a cross-linking agent for the polymerizable monomer) the precursor blend further may contain additional, optional, ingredients. These may comprise initiators, activators, pigments, fillers, radiopaquing agents, adhesion modifiers and other materials as will occur to those skilled in the art. Thus, it is useful to include free radical or photochemical initiators in the precursor blend composition of the invention to cause modification of the hardening kinetics thereof. In this regard, peroxy type initiators such as dicumyl or benzoyl peroxide are useful. Similarly, pigments and fillers may be added to modify the appearance, density, and physical characteristics of the resultant dental appliances. Inorganic materials, especially silica and titania, are useful fillers and pigments while a wide variety of other useful pigments and fillers will be apparent to those skilled in the art. While, in general, fillers and radiopaquing agents may constitute a major part by weight of the precursor blend compositions of the invention, the initiators, activators, pigments, and adhesion modifiers should, taken as a whole, constitute a minor proportion by weight of the precursor blend compositions of which they are a part.

The precursor blends of the invention are formulated by a mixing together of the constituent species in proper proportion, followed by aging or maturing. Several techniques are available for this and others will be apparent to those skilled in the art. Thus, it is possible to combine cross-linked polymer, uncross-linked polymer, polymerizable monomer and a cross-linking agent for said monomer in proper proportions including therewith, for example, a peroxide initiator and a pigment. This combination is then thoroughly mixed and aged to result in a precursor blend which has a uniform appearance. This blend may have the consistency of dough or may be more or less mobile depending upon the desired use therefor. The precursor blend thus formed may be alternatively molded, extruded, brushed, formed, worked or otherwise shaped in any conventional manner and caused to polymerize or cure to result in hard dental appliances having superior properties. The application of heat or radiant energy is usually required, for this polymerization or curing.

It is especially useful to mold precursor blends into artificial teeth for inclusion in prosthetic devices. It is to be understood, however, that the precursor blends are suitable for a very wide range of dental uses, including fillings, teeth, bridges, crowns, facings, pit and fissure sealants, denture base and denture reline materials, orthodontic splint materials, and adhesives for orthodontic appliances. The materials of the invention may also be utilized for prosthetic replacement or repair of various hard body structures such as bone and may be utilized for reconstructive purposes during surgery, especially oral surgery.

The nature of the chemical and physical relationships among the components of the precursor blends of the invention is important to the practice of the invention. Chief among these relationships is the necessity that the cross-linked polymer particles be capable of swelling with or imbibing the monomer component of the invention. Of similar importance is the requirement that the uncross-linked polymers, when included, be capable of dissolving in the monomer component. In accordance with the invention, the precursor blend formed by any of the useful techniques described above is aged for a period of time sufficient to insure that the cross-linked polymer has become substantially fully swollen with, interpenetrated by or has substantially imbibed the monomer-cross-linking agent mixture, and that the uncross-linked polymer, if used, has substantially dissolved therein. Thus, as used herein, "aged" or "aging" refers to the maintenance of the components of the precursor blend in association with one another in the blend for a period of time sufficient to substantially fully swell the cross-linked polymer particles with the mixture of polymerizable monomer and cross-linking agent dissolved therein. Frequently, the aging process is manifested by a change in the consistency of the mixture as equilibrium is approached. The time necessary to approach such equilibrium will vary depending upon the blending techniques, the relative proportions of materials, the particle sizes and molecular weights of the polymers and the temperature extant in the mixtures. In general, aging time of from one to seven days has been found to be adequate to approach the desired equilibrium. It is to be understood that it lies well within the abilities of those skilled in the art to ascertain the optimum aging time for a formulation in view of the foregoing considerations.

A further technique especially useful for the formulation of the precursor blends of the invention, denominated as the preswell method, causes the cross-linked polymer particles to swell with or imbibe a mixture of polymerizable monomer and cross-linking agent for said monomer at a time remote from and preceding the final mixing of the ultimate precursor blend. In accordance with this preferred technique, the cross-linked polymer particles are blended with a mixture of polymerizable monomer and cross-linking agent (dissolved in said monomer). The blend is then aged for a period of time sufficient to permit the cross-linked polymer particles to be substantially fully swollen with, or interpenetrated by the monomer-cross-linking agent mixture. In general, an amount of monomer is selected which will be completely imbibed by the cross-linked polymer particles with which the monomer is combined. This "preswollen" cross-linked polymer-monomer combination may subsequently be mixed with uncross-linked polymer and further quantities of polymerizable monomer and cross-linking agent to form the precursor blend. This technique affords savings in time and results in greater convenience in the formulation of the precursor blends of the invention due to the fact that aging has taken place in advance of final mixing. Precursor blends thus formed may be alternatively molded, brushed, extruded, formed, worked or otherwise shaped in manners similar to those useful with batch mixing techniques to form similarly useful articles. Other techniques are presented in the examples which follow, and still others will be apparent to those skilled in the art.

Upon polymerization of the precursor blends, a three dimensional structure is believed to be formed which may be denominated as an interpenetrating polymeric network or IPN. The IPN structure which is thought thus to form is believed to be a major contributing factor to the serendipitous combination of superior chemical and physiochemical properties which is exhibited by the articles constructed according to the practice of the invention. Interpenetrating polymeric networks are related to, but distinct from, traditional graft polymers. In general, when a second polymer is synthesized in the intimate presence of a first polymer, the resultant material has been known as a graft polymer regardless of the actual extent of chemical grafting of one polymer to the other. IPN's are thought to be formed, however, when the first polymer is substantially cross-linked into a three dimensional network prior to the formation of the second polymer, and when that second polymer is caused to form in such a fashion that it too is substantially cross-linked into a three dimensional network.

Thus, an IPN may be viewed as being composed of two or more cross-linked, and hence three dimensionally arrayed, polymeric networks which co-exist in the same volume of space, but which do not necessarily have any covalent bonds in common. While the two networks may, indeed, be independent in the sense that they need posess no covalent linkages between them; they are physically trapped one "within" the other and cannot disassociate by any physical manipulation without the rupture of covalent bonds.

Central to an understanding of interpenetrating polymeric networks is the recognition that an IPN is not a substance per se, but is, rather, a term descriptive of a structure. For discussions of the nature of IPN's in general, see the recent papers by L. H. Sperling et al, Macromolecules, vol. 9, No. 4 (1976); Macromolecules, vol. 9, No. 5 (1976); J Polymer Science, vol. 12, page 141 (1977); and J Polymer Science, vol. 16, page 583 (1978); and articles cited therein. Also, see Klepner et al, J Elastoplast, vol. 5, page 196 (Oct. 1973).

While it appears to be desirable that the cross-linking of both polymers be substantial, various degrees of cross-linking are possible in both the preformed polymer and the polymer formed in situ. In addition, it should be recognized that an IPN may be formed even when the initial and second polymers are formed from the same materials. For example, two independent networks of a polymethacrylate, suitably cross-linked, may interpenetrate each other to form an IPN. Similarly, an IPN need not be limited only to two networks, as mixtures of two or more polymers may be used as the initial polymer, and mixtures of two or more monomers may be employed to form a second polymeric network. Mixtures of two or more cross-linking agents may also be used in either network formation.

It is thought that in the present invention, interpenetrating polymeric networks may be formed. Thus, when particulate cross-linked polymer is allowed to swell with or imbibe monomer mixed with cross-linking agent, and when the imbibed mixture of monomer and cross-linking agent is subsequently caused to polymerize, an interpenetrating polymeric network may be seen to be formed within the confines of the particulate cross-linked polymer. It is believed that it is this interpenetrating polymeric network structure, which is localized in the particulate masses formed subsequent to the swelling of particulate cross-linked polymer and the polymerization of the precursor blend, that lends the superior chemical and physiochemical properties to the articles formed according to this invention. It is believed that the aging process employed in the preparation of the precursor blends of the invention is required to accomplish substantially full swelling with, interpenetration by or substantially completeinbibition of monomer-cross-linking agent by the cross-linked polymer particles, and to approach an equilibrium thereof. It is to be understood, however, that the foregoing discussion of interpenetrating polymeric networks and their application to the present invention is not to be construed as a limiting factor thereof, but, rather, is to be interpreted as a mechanism which is proposed as being applicable in the present case.

As has been indicated, the compositions of the invention exhibit superior chemical and physiochemical properties. Accordingly, the articles made from the compositions of the invention exhibit superior grind resistance, monomer resistance, and bonding strength to denture bases. In addition, such articles display a unique microstructure.

Prosthetic Teeth

EXAMPLE 1

A precursor blend was prepared from the following composition:

| | |
|---|---|
| 47.83% | methyl methacrylate |
| 0.17% | benzoyl peroxide |
| 12.00% | 2,2-bis (4-methacryloxyphenyl)propane |
| 25.80% | poly (methyl methacrylate-co-ethylene dimethacrylate) (98.4:1.6) |
| 12.40% | poly(methyl methacrylate) |
| 1.80% | pigment |
| 100.00% | |

The cross-linked polymer was in the form of particles, 46% by weight of which were below 74 microns in size, the balance being below about 500 microns in size. The poly (methyl methacrylate) had an average molecular weight of 800,000 g/mole.

The benzoyl peroxide and 2,2-bis(4-methacryloxyphenyl)-propane were dissolved in the methyl methacrylate at ambient temperature to form a monomer solution. The polymers and pigment were charged to a planetary dough mixer containing the monomer solution and the charge was stirred until visibly homogeneous. Prosthetic teeth were injection molded by metered injection of polymerizable materials such that the tooth body builds up from the outside to the inside. The outer and inner external layers are formed first from the precursor blend from which polymer is omitted. The core is formed from the resultant precursor blend mixture after it was aged at ambient temperature for seven days. The resulting teeth grind with a dusty, fine debris, bond to denture base and are impact and wear resistant.

EXAMPLE 2

The method described in Example 1 was used to prepare a precursor blend from which prosthetic teeth were molded having the following composition:

A suitable gel-like consistency for molding prosthetic teeth was obtained after aging at ambient temperature for 24 hours.

EXAMPLE 3

The following composition yielded a precursor blend which could be molded into prosthetic teeth after processing according to the technique of Example 1:

EXAMPLE 4

A two-step "preswell" mixing method was used to prepare a precursor blend from which prosthetic teeth were molded, said blend having the following composition:

The cross-linked polymer was in the form of particles, 50% by weight of which were below 100 microns in size, the balance being below about 500 microns in size.

The poly(methyl methacrylate) had an average molecular weight of 850,000 g/mole.

The weight ratio of Step 1 to Step 2 material in this example is 1.14 to 1.00. Step 1 was achieved by preparing a solution of the monomers, crosslinkers and initiator and adding the cross-linked copolymer. This mixture was stirred for about two minutes to wet the polymer, capped against monomer loss, and held for one week at ambient temperature. The cross-linked copolymer completely absorbed the monomer solution during the one week "preswell" period. Although the copolymer was swollen by this process, the integrity of the individual copolymer particles was maintained. This "preswell" mixture was not gel-like, but had the consistency of a rubbery, spongy mass which was easily crumbled.

Step 2 was achieved by charging the "preswell", obtained in Step 1, to a planetary dough mixer and mixing sufficiently so as to break the "preswell" mass down to a fine consistency. The poly(methyl methacrylate) and pigment were added to the mixer and mixing was continued until a homogeneous dispersion was obtained. The solution of monomer and initiator, cited in the Step 2 composition, was charged to the mixer; mixing continued until a homogeneous, gel consistency was obtained. The gel-like mix was transferred to a holding container and aged at ambient temperature until a suitable consistency for molding prosthetic teeth was obtained, approximately three days.

EXAMPLE 5

The two-step "preswell" method described in Example 4, was used to prepare a precursor blend from which prosthetic teeth were molded having the following composition:

The weight ratio of Step 1 to Step 2 material in this example is 0.46 to 1.00. A suitable gel-like consistency for molding prosthetic teeth was obtained after aging at ambient temperature for 24 hours.

EXAMPLE 6

A precursor blend was prepared from the following composition:

The methyl methacrylate, benzoyl peroxide, and ethylene 'glycol' dimethacrylate were mixed at ambient temperature to form a monomer solution. The polymer and pigment were charged to a planetary dough mixer containing the monomer solution and then mixed until visibly homogeneous. The polymer completely imbibed the monomer solution during the first seven days of contact at ambient temperature in a sealed container; aging was continued for seven days prior to molding. Monolithic anterior prosthetic teeth were transfer molded by the following sequence:

1. 3 min. at 138.degree. C., 290 psi.
2. 2 min. at 138.degree. C., 1300 psi.
3. 5 min. cool at 1300 psi.
4. 3 hr. at 118.degree. C.

The resultant prosthetic teeth grind with a fine dusty debris, repolish to a high gloss, resist wear, resist methyl methacrylate and other solvents, are hydrolytically stable, show no visible degradation or distortion when heated at 220.degree. C. for one hour, and bond well to denture base material.

It will be apparent to those skilled in the art that various modifications and changes may be made in the practice and use of the present invention without departing from the scope thereof as set forth in the following claims.

What is claimed is:

1. Process for producing an artificial tooth comprising:
    injection molding a first portion of polymerizable material into a mold, and polymerizing said first portion of polymerizable material to form a first external polymeric layer (3)

injection molding a second portion of polymerizable material onto said first external polymeric layer, and polymerizing said second portion of polymerizable material to form an inner polymeric layer (2) applied on the first external layer (3) and injection molding a third portion of polymerizable material onto said inner layer, and polymerizing said third portion of polymerizable material, to form a solid core (1) applied on the inner layer (2), said polymerizable material comprising a blend of:
- (A) from 0% to about 50% of an uncross-linked polymer capable of dissolving in component (B);
- (B) from about 20% to about 66% of a monofunctional polymerizable monomer;
- (C) from about 10% to about 70% of a cross-linked polymer in the form of discrete particles having average diameters up to about 500 microns and being swellable in said monomer; and
- (D) from about 7% to about 27% of a di- or polyfunctional cross-linking agent reactive with said polymerizable monomer;

said percentages being based upon the total weight of A, B, C and D in said composition, said composition being capable of being hardened into a water insensitive object.

2. The process of claim 1 wherein the tooth is produced in a single injection process by controlled, metered injection of several polymerizable components such that the tooth body builds up from the outside to the inside.

3. The process according to claim 1, characterized in that multiple teeth, are injection-molded by means of one injection molding tool.

4. The process of claim 1 wherein a family of prosthetic teeth is formed by said process, said family of prosthetic teeth comprising a first tooth in a first set of teeth having a first ratio of the shade layer length (S) to back length (B) and a second tooth in a second set of teeth having a second ratio of the shade layer length to back length, said first and second ratios being substantially equal.

5. The process of claim 4 wherein said end of first and second tooth is an incisor and said first ratio is within 5 percent of being equal to said second ratio.

6. The process of claim 1 wherein a family of prosthetic teeth is formed by said process, said family of prosthetic teeth, comprising:

a first tooth in a first set of teeth, said first tooth having a first overall labial length (L), and a first back length (B), and a second tooth in a second set of teeth, said second tooth having a second overall labial length, and a second back length, the ratio of the first overall labial length to the second overall labial length being substantially equal to the ratio of the first back length to the second back length.

7. The process of claim 6 wherein said first tooth has a first shader length and said second tooth has a second length and the ratio of said first shader length to said first overall labial length is substantially equal to the ratio of said second shader length to said second overall labial length.

8. The process of claim 7 wherein each said tooth is a molar.

9. The process of claim 7 wherein each said tooth is an incisor.

10. The process of claim 7 wherein each said tooth is a canine.

11. The process of claim 7 wherein said first shader length is substantially equal to 68 percent of said first overall labial length.

12. The process of claim 6 wherein the ratio of the first overall labial length to the second overall labial length is within 5 percent of being equal to the ratio of the first back length to the second back length.

13. The process of claim 6 wherein each said tooth is an incisor.

14. The process of claim 6 wherein each said tooth is a canine.

15. The process of claim 6 wherein said first back length is substantially equal to 94 percent of said first overall labial length.

16. The process of claim 1 wherein said cross-linked polymer is present in an amount of from about 13% to about 52% by weight.

17. The process of claim 1 wherein said uncross-linked polymer is present in an amount of from about 13% to about 34% by weight.

18. The process of claim 1 wherein said polymerizable monomer is present in an amount of from about 25% to about 55% by weight.

* * * * *